(12) United States Patent
Eckhardt et al.

(10) Patent No.: US 9,127,034 B2
(45) Date of Patent: Sep. 8, 2015

(54) PROCESSES FOR PREPARING OF GLUCOPYRANOSYL-SUBSTITUTED BENZYL-BENZENE DERIVATES AND INTERMEDIATES THEREIN

(75) Inventors: Matthias Eckhardt, Biberach (DE); Frank Himmelsbach, Mittelbiberach (DE); Xiao-jun Wang, Danbury, CT (US); Wenjun Tang, Southbury, CT (US); Xiufeng Sun, Monroe, CT (US); Li Zhang, New Milford, CT (US); Dhileepkumar Krishnamurthy, Brookfield, CT (US); Christopher Hugh Senanayake, Brookfield, CT (US); Zhengxu Han, Shrewsbury, MA (US)

(73) Assignee: BOEHRINGER INGELHEIM INTERNATIONAL GMBH, Ingelheim (DE)

( * ) Notice: Subject to any disclaimer, the term of this patent is extended or adjusted under 35 U.S.C. 154(b) by 837 days.

(21) Appl. No.: 12/789,859

(22) Filed: May 28, 2010

(65) Prior Publication Data
US 2010/0240879 A1    Sep. 23, 2010

Related U.S. Application Data

(62) Division of application No. 11/416,683, filed on May 3, 2006, now Pat. No. 7,772,191.

(30) Foreign Application Priority Data

| May 10, 2005 | (EP) | 05010115 |
| Aug. 23, 2005 | (EP) | 05018265 |
| Sep. 15, 2009 | (EP) | 05108484 |

(51) Int. Cl.
| C07D 307/32 | (2006.01) |
| C07C 49/786 | (2006.01) |
| C07C 41/05 | (2006.01) |
| C07C 43/184 | (2006.01) |
| C07C 43/205 | (2006.01) |
| C07C 25/06 | (2006.01) |
| C07H 15/203 | (2006.01) |

(52) U.S. Cl.
CPC .................... C07H 15/203 (2013.01)

(58) Field of Classification Search
None
See application file for complete search history.

(56) References Cited

U.S. PATENT DOCUMENTS

| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,880,289 A | 3/1999 | Kaneko et al. |
| 6,414,126 B1 | 7/2002 | Ellsworth et al. |
| 6,515,117 B2 | 2/2003 | Ellsworth et al. |
| 6,613,806 B1 * | 9/2003 | Aven et al. ............. 514/687 |
| 6,627,611 B2 | 9/2003 | Tomiyama et al. |
| 6,774,112 B2 | 8/2004 | Gougoutas |
| 6,794,480 B2 * | 9/2004 | Goto et al. ............. 528/125 |
| 6,936,590 B2 | 8/2005 | Washburn et al. |
| 6,972,283 B2 | 12/2005 | Fujikura et al. |
| 7,169,761 B2 | 1/2007 | Tomiyama et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 * | 8/2009 | Eckhardt et al. ............. 536/1.11 |

(Continued)

FOREIGN PATENT DOCUMENTS

| CA | 2382480 A1 | 3/2001 |
| CA | 2388818 A1 | 4/2001 |

(Continued)

OTHER PUBLICATIONS

Ghassemi et al., "Synthesis and properties of new sulfonated poly(p-phenylene) derivatives for proton exchange membranes" Polymer (2004) vol. pp. 5847-5854.*

(Continued)

*Primary Examiner* — Eric Olson
(74) *Attorney, Agent, or Firm* — Michael P. Morris; Edouard G. Lebel

(57) ABSTRACT

The present invention relates to processes for preparing the compounds of general formula I,

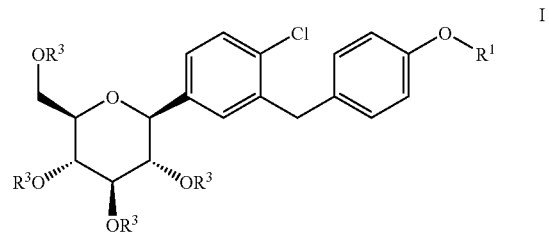

wherein the groups $R^1$ and $R^3$ are defined according to claim 1. Furthermore this inventions relates to intermediates obtained in these processes.

6 Claims, No Drawings

(56) References Cited

U.S. PATENT DOCUMENTS

| | | |
|---|---|---|
| 7,589,193 B2 | 9/2009 | Washburn et al. |
| 7,662,790 B2 | 2/2010 | Himmelsbach et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 2002/0137903 A1 | 9/2002 | Ellsworth et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0138148 A1 | 7/2004 | Fushimi et al. |
| 2004/0138439 A1 | 7/2004 | Deshpande et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0077212 A1 | 3/2011 | Seed et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0041069 A1 | 2/2012 | Sesha |
| 2012/0071403 A1 | 3/2012 | Strumph et al. |
| 2012/0196812 A1 | 8/2012 | Eickelmann et al. |
| 2012/0219622 A1 | 8/2012 | Kohlrausch et al. |
| 2012/0283169 A1 | 11/2012 | Grempler et al. |
| 2012/0296080 A1 | 11/2012 | Eckhardt et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |

FOREIGN PATENT DOCUMENTS

| | | |
|---|---|---|
| CA | 2402609 A1 | 9/2001 |
| CA | 2423568 A1 | 4/2002 |
| CA | 2437240 A1 | 8/2002 |
| CA | 2494177 A1 | 2/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2651019 A1 | 11/2007 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| WO | 9831697 A1 | 7/1998 |
| WO | 0116147 A1 | 3/2001 |
| WO | 0127128 A1 | 4/2001 |
| WO | 0174834 A1 | 10/2001 |

(56) References Cited

FOREIGN PATENT DOCUMENTS

| | | |
|---|---|---|
| WO | 02064606 A1 | 8/2002 |
| WO | 2002083066 A2 | 10/2002 |
| WO | 2003020737 A1 | 3/2003 |
| WO | 2003031458 A1 | 4/2003 |
| WO | 03078404 A1 | 9/2003 |
| WO | 2003099836 A1 | 12/2003 |
| WO | 2004007517 A1 | 1/2004 |
| WO | 2004013118 A1 | 2/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 9/2004 |
| WO | 2005012318 A2 | 2/2005 |
| WO | 2005012326 A1 | 2/2005 |
| WO | 2005021566 A2 | 3/2005 |
| WO | 2005063785 A2 | 7/2005 |
| WO | 2005085237 A1 | 9/2005 |
| WO | 2005085265 A1 | 9/2005 |
| WO | 2005092877 A1 | 10/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006064033 A2 | 6/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2008020011 A1 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2010045656 A2 | 4/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012062698 A1 | 5/2012 |
| WO | 2012107476 A1 | 8/2012 |
| WO | 2012120040 A1 | 9/2012 |

OTHER PUBLICATIONS

Revesz et al., "SAR of benzoylpyridines and benzophenones as p38a MAP kinase inhibitors with oral activity" Bioorganic and Medicinal Chemistry Letters (2004) vol. 14 pp. 3601-3605.*
Non-Final Office Action dated May 8, 2008 from U.S. Appl. No. 11/359,846, filed Feb. 22, 2006.
Notice of Allowance and Fee(s) Due dated Jan. 13, 2009 from U.S. Appl. No. 11/304,284, filed Dec. 15, 2005.
Notice of Allowance and Fee(s) Due dated Dec. 30, 2008 from U.S. Appl. No. 11/674,839, filed Feb. 14, 2007.
Notice of Allowance and Fee(s) Due dated Feb. 3, 2009 from U.S. Appl. No. 11/359,846, filed Feb. 22, 2006.
Notice of Allowance and Fee(s) Due dated Jan. 2, 2009 from U.S. Appl. No. 11/742,612, filed May 1, 2007.
Oku, Akira., et al; T-1095, An Inhibitor or renal Na+-Glucose Cotransporters, May Provide a Novel Approach to Treating Diabetes; Diabetes (1999) vol. 48 pp. 1794-1800.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Piya, Milan K. et al. "Emerging treatment options for type 2 diabetes" British Journal of Clinical Pharmacology, (2010) vol. 70, No. 5, pp. 631-644.
Printz, Richard L. et al. "Tweaking the Glucose Sensor: Adjusting Glucokinase Activity with Activator Compounds" Endocrinology, (2005) vol. 146, No. 9, pp. 3693-3695.
Rainier, Jon D. et al. "Aluminum- and Boron-Mediated C-Glycoside Synthesis from 1 2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Response filed dated Nov. 5, 2008 to Non-Final Office Action dated May 8, 2008 from U.S. Appl. No. 11/359,846, filed Feb. 22, 2006.
Response dated Sep. 25, 2008 to Non-Final Office Action dated Apr. 2, 2008 from U.S. Appl. No. 11/674,839, filed Feb. 14, 2007.
Response dated Sep. 25, 2008 to Non-Final Office Action dated Apr. 2, 2008 from U.S. Appl. No. 11/742,612, filed May 1, 2007.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Sherwin, Robert S. et al. "The Prevention or Delay of Type 2 Diabetes" Diabetes Care, (2002) vol. 25, No. 4, pp. 742-749.
Silverman, et al. "Handbook of Grignard Reagents" Marcel Dekker (1996) p. 82.
Singhal, Dharmendra et al. "Drug polymorphism and dosage form design: a practical perspective" Advanced Drug Delivery Reviews, 56, (2004) pp. 335-347.
Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.
Stazi, Federica., et al; Statistical Experimental Design-Driven Discovery of room-Temperature Conditions for Cyanation of Aryl Bromides; Tetrahedron Letters (2005) vol. 46 1815-1818; Elsevier Ltd.
Tanaka, Chikako "Therapeutic Drugs for Metabolic Diseases, Chapter 2" (2002) New Yakurigaku (New Pharmacology) pp. 524-527.
Threlfall, Terry "Structural and Thermodynamic Explanations of Ostwald's Rule" Organic Process Research & Development (2003) vol. 7, pp. 1017-1027.
Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.
U.S. Appl. No. 13/367,739, filed Feb. 7, 2012. Inventor: Thomas Klein.
U.S. Appl. No. 13/413,702, filed Mar. 7, 2012. Inventor: Masanori Ito.

(56) References Cited

OTHER PUBLICATIONS

U.S. Appl. No. 13/637,413, filed Sep. 26, 2012. Inventor: Rolf Grempler.
U.S. Appl. No. 13/693,239, filed Dec. 4, 2012. Inventor: Klaus Dugi.
Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
Wallace, Debra J., et al; Cyclopropylboronic Acid: Synthesis and Suzuki Cross-Coupling Reactions; Tetrahedron Letters (2002) vol. 43 pp. 6987-6990; Pergamon Press.
Websters Third New International Dictionary, Editor: GOVE, definition of prevent; 1963, 2 pgs.
Xue, Song., et al; Zinc-mediated Synthesis of Alpha-C-Glycosided from 1,2-Anhydroglycosides; Synletters (2003) vol. 6 pp. 870-872.
Yamada, Yuichiro et al. "Clinic: Careful Progress in the Field and new Therapeutic Methods" Medical Online, (2007) vol. 220, No. 13, pp. 1219-1221.
Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Ault Addison, "Techniques and experiments for organic chemistry" University Science Books, 1998, pp. 59-60.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Byrn, Stephen et al. "Pharmaceutical Solids: A Strategic Approach to Regulatory Considerations" Pharmaceutical Research, vol. 12, No. 7, (1995) pp. 945-954.
Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.
Drug Watch "Type 2 Diabetes Mellitus" Formulary vol. 43 Aug. 2008 p. 304.
Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.
Fujimori, Yoshikazu et al. "Remogliflozin Etabonate in a Novel Category of Selective Low-Affinity Sodium Glucose. Cotransporter (SGLT2) Inhibitors, Exhibits Antidiabetic Efficacy in Rodent Models" (2008) Journal of Pharmacology and Experimental Therapeutics vol. 327 No. 1, pp. 268-276.
Greco, Gary T. et al. "Segregation of Active Constituents from Tablet Formulations During Grinding: Theoretical Considerations" Drug Development and Industrial Pharmacy, (1982) 8(4), pp. 565-578.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Hutton, Craig A., et al; A Convenient Preparation of dityrosine Via Miyaura Borylation-Suzuki Coupling of IodotyrosineDerivatives; Tetrahedron Letters (2003) vol. 44 pp. 4895-4898; Pergamon Press.
Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
International Search Report for PCT/EP2005/002618 mailed Jun. 30, 2005.
International Search Report for PCT/EP2005/056806 mailed Dec. 27, 2006.
International Search Report for PCT/EP2006/061520 mailed Jul. 26, 2006.
International Search Report for PCT/EP2006/061956 mailed on Jul. 5, 2006.
International Search report for PCT/EP2006/061957 mailed on Jul. 5, 2006.
International Search Report for PCT/EP2006/062191 mailed Aug. 8, 2006.
International Search Report for PCT/EP2006/064702 mailed on Jul. 26, 2007.
International Search Report for PCT/EP2006/065710 mailed Mar. 8, 2007.
International Search Report for PCT/EP2006/066107 mailed Jan. 11, 2007.
International Search Report for PCT/EP2006/066347 mailed Mar. 7, 2007.
International Search Report for PCT/EP2007/051411 mailed on May 2, 2007.
International Search Report for PCT/EP2007/054248 mailed on Jun. 18, 2007.
International Search Report for PCT/EP2010//064117 mailed on Nov. 30, 2010.
International Search Report for PCT/EP2010/064120 mailed Mar. 31, 2011.
Isaji, Masayuki "Sodium-glucose cotransporter inhibitors for diabetes" Current Opinion in Investigational Drugs, (2007) vol. 8, No. 4, pp. 285-292.
Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.
Knochel, Paul et al. "Highly functionalized Organomagnesium Reagents Prepared through Halogen-Metal Exchange" Angew. Chem. INt. Ed. (2003) vol. 42, 4302-4320.
Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.
Krasovskiy Arkady et al. "A LiCL-Mediated Br/Mg Exchange Reaction for the Preparation of Functionalized Aryl-and Heterarylmagnesium Compounds from Organic Bromides" Angew. Chem. Int. Ed. (2004) vol. 43, pp. 3333-3336.
Kuribayashi, Takeshi., et al; Bis C-Glycosylated Diphenylmethanes for Stable Glycoepitope Mimetics; Syntletters (1999) vol. 6 pp. 737-740.
Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.
Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.
Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
Lipworth, Brian J. "Clinical pharmacology of b3-adrenoceptors" Br J Clin Pharmacol (1996) pp. 291-300.
McHale, Mary "Grignard Reaction" Connexions module: m15245, (2007) pp. 1-18.
McLaughlin, Mark., et al; Suzuki-Miyaura Cross-Coupling of Benzylic Phosphates with Arylboronic Acids; Organic Letters (2005) vol. 7 No. 22 pp. 4875-4878.
McMaster University, Chem2006 Lab Manual, 1997198, Expt 1, Part B, pp. 1-9.

(56) References Cited

OTHER PUBLICATIONS

Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.

Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.

Merriam-Webster's Collegiate Dictionary, published 1998 by Merriam-Webster Inc. p. 924.

Neamati, Ouri., et al; "Depsides and Depsidones as Inhibition of HIV-1 Integrase: Dimvery of Novel Inhibitors Through 3D Database Searclung", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Non Final Office Action dated Apr. 2, 2008 from U.S. Appl. No. 11/674,839, filed Feb. 14, 2007.

Non Final Office Action dated Apr. 2, 2008 from U.S. Appl. No. 11/742,612, filed May 1, 2007.

Non-Final Office Action dated Jun. 24, 2008 from U.S. Appl. No. 11/406,971, filed Apr. 19, 2006.

Non-Final Office Action dated Jun. 5, 2008 from U.S. Appl. No. 11/408,899, filed Apr. 21, 2006.

Castelhano, Arlindo L. et al. "Reactions of an Electrophilic Glycine Cation Equivalent With Grignard Reagents a Simple Synthesis of $\beta,g$-Unsaturated Amino Acids" (1986) Tetrahedron Letters, vol. 27, No. 22, pp. 2435-2438.

Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.

Tsujihara, Kenji et al. "Na+-Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.

\* cited by examiner

PROCESSES FOR PREPARING OF GLUCOPYRANOSYL-SUBSTITUTED BENZYL-BENZENE DERIVATES AND INTERMEDIATES THEREIN

This application is a Divisional of U.S. application Ser. No. 11/416,683, filed May 3, 2006, which claims priority to EP 05010115, filed May 10, 2005; EP05018265, filed Aug. 23, 2005; and EP 05108484, filed Sep. 15, 2005, the contents of which are incorporated herein in their entireties.

The present invention relates to a process for preparing of glucopyranosyl-substituted benzyl-benzene derivatives of the formula I,

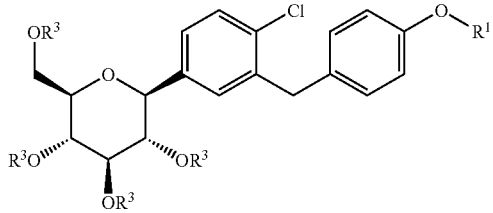

wherein the substituents $R^1$ and $R^3$ are defined as hereinafter. Furthermore the present invention relates to processes for preparing intermediates and starting materials of the process for preparing of glucopyranosyl-substituted benzyl-benzene derivatives. In addition the present invention relates to such intermediates and starting material.

BACKGROUND OF THE INVENTION

In the international patent application WO 2005/092877 glucopyranosyl-substituted benzene derivatives of the general formula

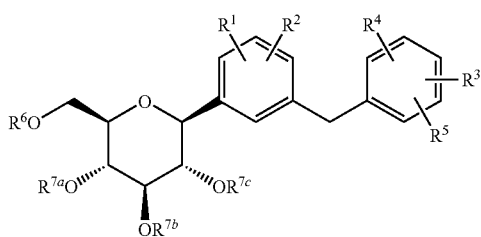

wherein the groups $R^1$ to $R^6$ and $R^{7a}$, $R^{7b}$, $R^{7c}$ are as defined therein, are described. Such compounds have a valuable inhibitory effect on the sodium-dependent glucose cotransporter SGLT, particularly SGLT2.

AIM OF THE INVENTION

The aim of the present invention is to find new processes for preparing of glucopyranosyl-substituted benzyl-benzene derivatives of the formula I; in particular processes with which the product may be obtained in high yields, high enantiomeric or diastereomeric purity and which allow the manufacture of the product in a commercial scale with a low technical expenditure and a high space/time yield.

Another aim of the present invention is to provide processes for preparing the starting materials of the beforementioned method of manufacture.

Further aims of the present invention relate to new intermediates and starting materials in the process according to the present invention.

Other aims of the present invention will become apparent to the skilled artisan directly from the foregoing and following description.

OBJECT OF THE INVENTION

In a first aspect the present invention relates to a process for preparing the compounds of general formula I,

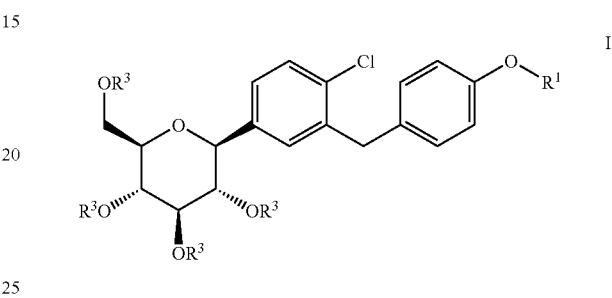

wherein $R^1$ denotes cyclobutyl, cyclopentyl, cyclohexyl, R-tetrahydrofuran-3-yl, S-tetrahydrofuran-3-yl or tetrahydropyran-4-yl; and $R^3$ denotes hydrogen;

characterised in that in a compound of general formula II

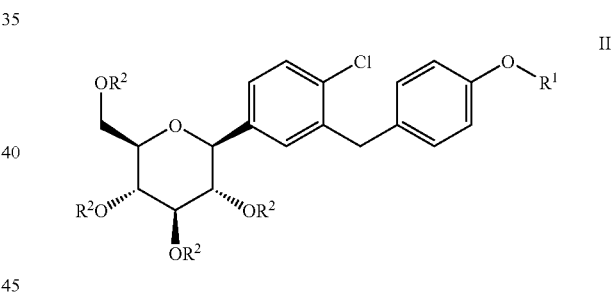

wherein $R^1$ is defined as hereinbefore and $R^2$ independently of one another denote hydrogen, ($C_{1-18}$-alkyl)carbonyl, ($C_{1-18}$-alkyl)oxycarbonyl, arylcarbonyl, aryl-($C_{1-3}$-alkyl)-carbonyl, aryl-$C_{1-3}$-alkyl, allyl, $R^aR^bR^cSi$, $CR^aR^bOR^c$, wherein two adjacent groups $R^2$ may be linked with each other to form a bridging group $SiR^aR^b$, $CR^aR^b$ or $CR^aOR^b$—$CR^aOR^b$; with the proviso that at least one substituent $R^2$ is not hydrogen;

$R^a$, $R^b$, $R^c$ independently of one another denote $C_{1-4}$-alkyl, aryl or aryl-$C_{1-3}$-alkyl, while the alkyl may be mono- or polysubstituted by halogen;

L1 independently of one another are selected from among fluorine, chlorine, bromine, $C_{1-3}$-alkyl, $C_{1-4}$-alkoxy and nitro;

while by the aryl groups mentioned in the definition of the above groups are meant phenyl or naphthyl groups, preferably phenyl groups, which may be mono- or polysubstituted with L1;

the protective groups $R^2$ not being hydrogen are cleaved, in particular hydrolysed.

In a second aspect the present invention relates to a process for preparing the compounds of general formula II,

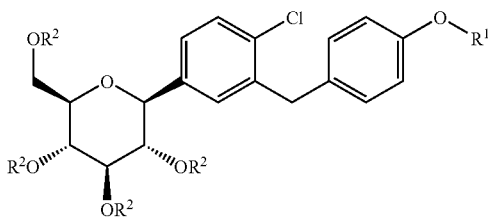

wherein
R¹ denotes cyclobutyl, cyclopentyl, cyclohexyl, R-tetrahydrofuran-3-yl, S-tetrahydrofuran-3-yl or tetrahydropyran-4-yl; and
R² independently of one another denote hydrogen, ($C_{1-18}$-alkyl)carbonyl, ($C_{1-18}$-alkyl)oxycarbonyl, arylcarbonyl, aryl-($C_{1-3}$-alkyl)-carbonyl, aryl-$C_{1-3}$-alkyl, allyl, $R^aR^bR^cSi$, $CR^aR^bOR^c$, wherein two adjacent groups R² may be linked with each other to form a bridging group $SiR^aR^b$, $CR^aR^b$ or $CR^aOR^b$—$CR^aOR^b$;
$R^a$, $R^b$, $R^c$ independently of one another denote $C_{1-4}$-alkyl, aryl or aryl-$C_{1-3}$-alkyl, while the alkyl groups may be mono- or polysubstituted by halogen;
L1 independently of one another are selected from among fluorine, chlorine, bromine, $C_{1-3}$-alkyl, $C_{1-4}$-alkoxy and nitro;
while by the aryl groups mentioned in the definition of the above groups are meant phenyl or naphthyl groups, preferably phenyl groups, which may be mono- or polysubstituted with L1;
characterised in that a compound of general formula III

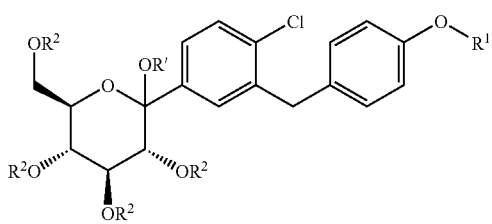

wherein R¹ and each R² are defined as hereinbefore and R' denotes hydrogen, $C_{1-6}$-alkyl, ($C_{1-4}$-alkyl)carbonyl, ($C_{1-4}$-alkyl)oxycarbonyl, arylcarbonyl, aryl-($C_{1-3}$-alkyl)-carbonyl; while the term "aryl" is defined as hereinbefore;
is reacted with a reducing agent.

In a third aspect the present invention relates to a process for preparing the compounds of general formula III,

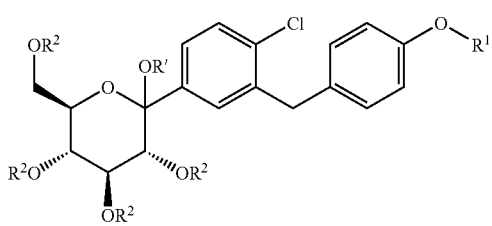

wherein
R¹ denotes cyclobutyl, cyclopentyl, cyclohexyl, R-tetrahydrofuran-3-yl, S-tetrahydrofuran-3-yl or tetrahydropyran-4-yl; and
R² independently of one another denote hydrogen, ($C_{1-18}$-alkyl)carbonyl, ($C_{1-18}$-alkyl)oxycarbonyl, arylcarbonyl, aryl-($C_{1-3}$-alkyl)-carbonyl, aryl-$C_{1-3}$-alkyl, allyl, $R^aR^bR^cSi$, $CR^aR^bOR^c$, wherein two adjacent groups R² may be linked with each other to form a bridging group $SiR^aR^b$, $CR^aR^b$ or $CR^aOR^b$—$CR^aOR^b$; and
$R^a$, $R^b$, $R^c$ independently of one another denote $C_{1-4}$-alkyl, aryl or aryl-$C_{1-3}$-alkyl, while the alkyl groups may be mono- or polysubstituted by halogen;
L1 independently of one another are selected from among fluorine, chlorine, bromine, $C_{1-3}$-alkyl, $C_{1-4}$-alkoxy and nitro;
R' denotes hydrogen, $C_{1-6}$-alkyl, ($C_{1-4}$-alkyl)carbonyl, ($C_{1-4}$-alkyl)oxycarbonyl, arylcarbonyl, aryl-($C_{1-3}$-alkyl)-carbonyl;
while by the aryl groups mentioned in the definition of the above groups are meant phenyl or naphthyl groups, preferably phenyl groups, which may be mono- or polysubstituted with L1;
characterised in that an organometallic compound of the formula VI

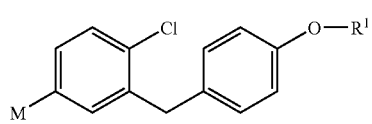

wherein R¹ is defined as hereinbefore and M denotes Li or MgHal, wherein Hal denotes Cl, Br or I;
or a derivative thereof obtained by transmetallation;
which compound of the formula VI may be obtained by halogen-metal exchange or by the insertion of a metal in the carbon-halogen bond of a halogen-benzylbenzene compound of general formula V

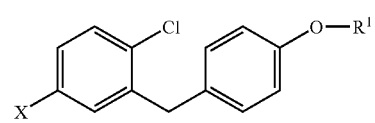

wherein R¹ is defined as hereinbefore and X denotes Br or I; and optionally subsequent transmetallation, is added to a gluconolactone of general formula IV

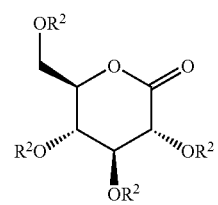

wherein R² is as hereinbefore defined,
then the adduct obtained is reacted with water or an alcohol R'—OH, where R' denotes $C_{1-6}$-alkyl, in the presence of an acid and optionally the product obtained in the reaction with water wherein R' denotes H is converted in a subsequent reaction with an acylating agent into the product of formula III wherein R' denotes $(C_{1-4}\text{-alkyl})$carbonyl, $(C_{1-4}\text{-alkyl})$oxy-carbonyl, arylcarbonyl or aryl-$(C_{1-3}\text{-alkyl})$-carbonyl, wherein the term "aryl" is defined as hereinbefore.

In a fourth aspect the present invention relates to a process for preparing the compounds of general formula XXXIII,

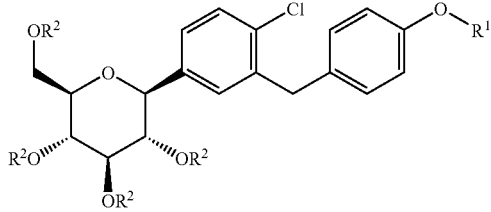

XXXIII wherein $R^1$, $R^2$ are defined as hereinbefore and hereinafter; characterised in that a protected D-glucal of the formula XXX

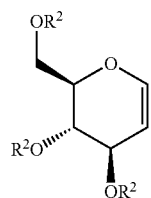

XXX wherein $R^2$ is defined as hereinbefore; is metallated to yield a metallated D-glucal of the formula XXXI

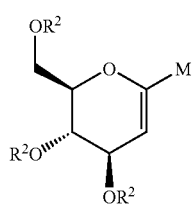

XXXI wherein $R^2$ is defined as hereinbefore and M denotes lithium or a magnesium moiety;
which is optionally transmetallated to yield a metallated D-glucal of the formula XXXI, wherein M denotes a magnesium, zinc, indium, boron, tin, silicon or chromium moiety; and
the metallated or trans-metallated D-glucal of the formula XXXI is reacted with an aglycon of the formula V

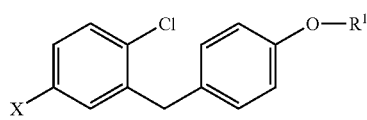

V wherein $R^1$ is defined as hereinbefore and X denotes a leaving group;
in the presence of a transition metal catalyst
to yield a glucal derivative of the formula XXXII

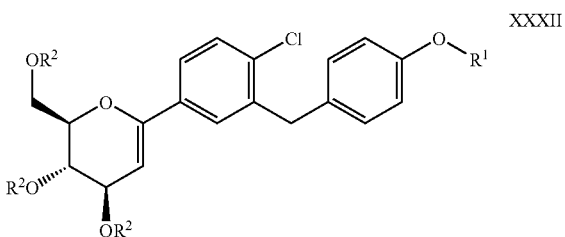

XXXII wherein $R^1$ and $R^2$ are defined as hereinbefore; and
the glucal derivative of the formula XXXII is converted to the product of the formula XXXIII by the addition of water to the double bond of the glucal moiety, in particular by hydroboration of the double bond and subsequent cleavage of the carbon-boron bond or by epoxidation or dihydroxylation of the double bond and subsequent reduction of the resultant anomeric carbon-oxygen bond.

In a fifth aspect the present invention relates to a process for preparing the compounds of general formula XXXIII,

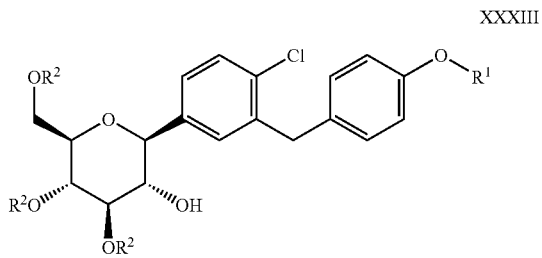

XXXIII wherein $R^1$, $R^2$ are defined as hereinbefore and hereinafter; characterised in that a protected D-glucal of the formula XXX

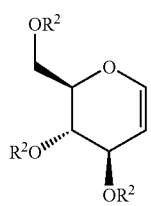

XXX wherein $R^2$ is defined as hereinbefore;
is epoxidated to yield the corresponding glucaloxide of the formula XXXIV

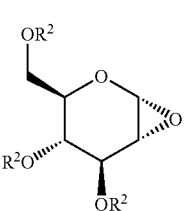

XXXIV wherein R² is defined as hereinbefore; and the glucaloxide of the formula XXXIV is reacted with a metallated aglycon of the formula VI

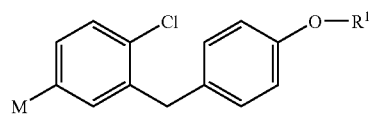

wherein R¹ is defined as hereinbefore and M denotes a lithium, magnesium, zinc, indium, aluminum or boron moiety;

to yield the product of the formula XXXIII.

In a sixth aspect the present invention relates to a process for preparing the compounds of general formula II,

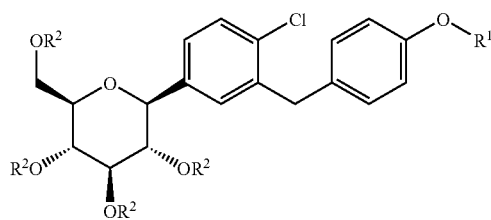

wherein R¹, R² are defined as hereinbefore and hereinafter;

characterised in that a glucose derivative of the formula XXXV

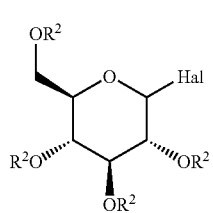

wherein R² is defined as hereinbefore and

Hal denotes F, Cl, Br, $C_{1-3}$-alkylcarbonyloxy, $C_{1-3}$-alkyloxycarbonyloxy or $C_{1-3}$-alkyloxy;

is reacted with a metallated aglycon of the formula VI

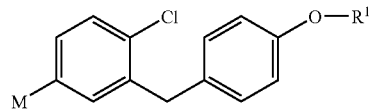

wherein R¹ is defined as hereinbefore and M denotes a lithium, magnesium, zinc, indium or boron moiety;

to yield the product of the formula II.

In a seventh aspect the present invention relates to a process for preparing the compounds of general formula V,

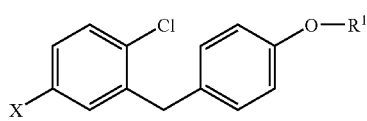

wherein

R¹ denotes cyclobutyl, cyclopentyl, cyclohexyl, R-tetrahydrofuran-3-yl, S-tetrahydrofuran-3-yl or tetrahydropyran-4-yl; and X denotes a bromine atom or an iodine atom;

characterised in that a benzoyl chloride derivative of the formula XII

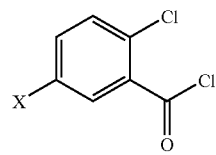

wherein X is defined as above; or a derivative thereof such as a benzoyl anhydride, an ester or a benzonitrile;

is reacted with a halobenzene of the formula XXVII

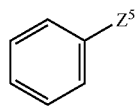

wherein Z⁵ denotes a fluorine, chlorine or iodine atom;

in the presence of a catalyst to obtain an intermediate compound of the formula XXVI

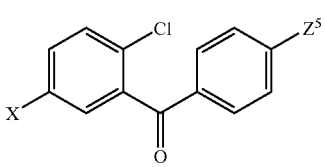

wherein X and Z⁵ are defined as hereinbefore; and the intermediate compound of the formula XXVI is reacted with R¹—OH, wherein R¹ is defined as hereinbefore, or an anion thereof, preferably in a solvent or mixture of solvents, in the presence of a base to yield a benzophenone derivative of the formula VII

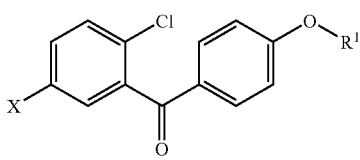

wherein X and R$^1$ are defined as hereinbefore; and the benzophenone derivative of the formula VII is reacted with a reducing agent, preferably in a solvent or mixture of solvents, in the presence of a Lewis acid to furnish the compound of the formula V as defined above.

In an eighth aspect the present invention relates to a process for preparing the compounds of general formula II,

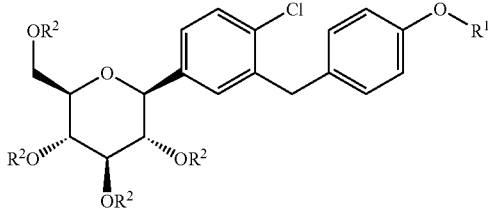

wherein R$^1$ and R$^2$ are defined as hereinbefore, characterized in that an aglycon of the formula V

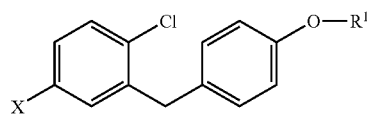

wherein X and R$^1$ are defined as hereinbefore, is obtained by a process according to the seventh aspect of this invention, and said halogen-benzylbenzene compound of general formula V is transformed into an organometallic compound of the formula VI

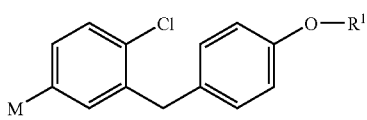

wherein R$^1$ is defined as hereinbefore and M denotes Li or MgHal, wherein Hal denotes Cl, Br or I;

P by an halogen-metal exchange or by the insertion of a metal in the carbon-halogen bond of the halogen-benzylbenzene compound of general formula V, and optionally subsequent transmetallation; and said organometallic compound of the formula VI is reacted with a gluconolactone of general formula IV

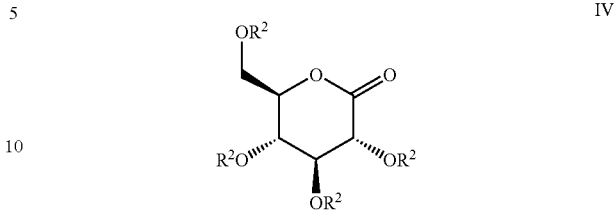

wherein R$^2$ is as hereinbefore defined, in accordance with the process of the third aspect of this invention to obtain an intermediate of the formula III,

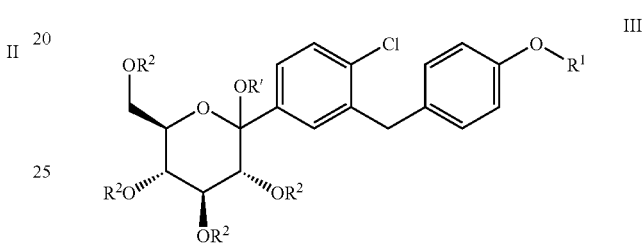

wherein R$^2$, R' and R$^1$ are defined as hereinbefore, and said intermediate of the formula III is reacted with a reducing agent in accordance with the second aspect of this invention to obtain the compound of the formula II.

In a ninth aspect the present invention relates to compounds of general formula II

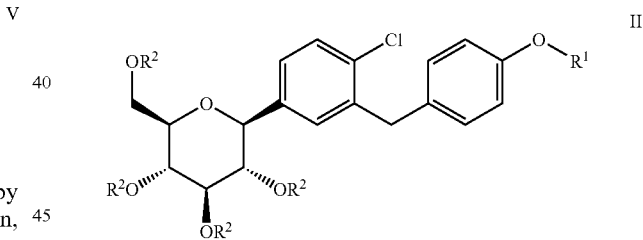

wherein
R$^1$ denotes cyclobutyl, cyclopentyl, cyclohexyl, R-tetrahydrofuran-3-yl, S-tetrahydrofuran-3-yl or tetrahydropyran-4-yl; and
R$^2$ independently of one another denote hydrogen, (C$_{1-18}$-alkyl)carbonyl, (C$_{1-18}$-alkyl)oxycarbonyl, arylcarbonyl, aryl-(C$_{1-3}$-alkyl)-carbonyl, aryl-C$_{1-3}$-alkyl, allyl, R$^a$R$^b$R$^c$Si, CR$^a$R$^b$OR$^c$, wherein two adjacent groups R$^2$ may be linked with each other to form a bridging group SiR$^a$R$^b$, CR$^a$R$^b$ or CR$^a$OR$^b$—CR$^a$OR$^b$; with the proviso that at least one substituent R$^2$ does not denote hydrogen;
R$^a$, R$^b$, R$^c$ independently of one another denote C$_{1-4}$-alkyl, aryl or aryl-C$_{1-3}$-alkyl, while the alkyl groups may be mono- or polysubstituted by halogen;
L1 independently of one another are selected from among fluorine, chlorine, bromine, C$_{1-3}$-alkyl, C$_{1-4}$-alkoxy and nitro; while by the aryl groups mentioned in the definition of the above groups are meant phenyl or naphthyl groups, preferably phenyl groups, which may be mono- or polysubstituted with L1.

In a further aspect the present invention relates to compounds of general formula III <chemical structure III> wherein

R¹ denotes cyclobutyl, cyclopentyl, cyclohexyl, R-tetrahydrofuran-3-yl, S-tetrahydrofuran-3-yl or tetrahydropyran-4-yl; and R² independently of one another denote hydrogen, ($C_{1-18}$-alkyl)carbonyl, ($C_{1-18}$-alkyl)oxycarbonyl, arylcarbonyl, aryl-($C_{1-3}$-alkyl)-carbonyl, aryl-$C_{1-3}$-alkyl, allyl, $R^aR^bR^cSi$, $CR^aR^bOR^c$, wherein two adjacent groups R² may be linked with each other to form a bridging group $SiR^aR^b$, $CR^aR^b$ or $CR^aOR^b$—$CR^aOR^b$;

$R^a$, $R^b$, $R^c$ independently of one another denote $C_{1-4}$-alkyl, aryl or aryl-$C_{1-3}$-alkyl, while the alkyl or aryl groups may be mono- or polysubstituted by halogen;

L1 independently of one another are selected from among fluorine, chlorine, bromine, $C_{1-3}$-alkyl, $C_{1-4}$-alkoxy and nitro;

R' denotes hydrogen, $C_{1-6}$-alkyl, ($C_{1-4}$-alkyl)carbonyl, ($C_{1-4}$-alkyl)oxycarbonyl, arylcarbonyl, aryl-($C_{1-3}$-alkyl)-carbonyl; while by the aryl groups mentioned in the definition of the above groups are meant phenyl or naphthyl groups, preferably phenyl groups, which may be mono- or polysubstituted with L1.

In a further aspect the present invention relates to compounds of general formula VI <chemical structure VI> wherein

R¹ denotes cyclobutyl, cyclopentyl, cyclohexyl, R-tetrahydrofuran-3-yl, S-tetrahydrofuran-3-yl or tetrahydropyran-4-yl; and M denotes Li or MgHal, wherein Hal denotes Cl, Br or I.

In a further aspect the present invention relates to compounds of general formula V <chemical structure V> wherein

R¹ denotes cyclobutyl, cyclopentyl, cyclohexyl, R-tetrahydrofuran-3-yl, S-tetrahydrofuran-3-yl or tetrahydropyran-4-yl; and X denotes Br or I.

In a further aspect the present invention relates to compounds of the formula VII <chemical structure VII> or of the formula XIX

<chemical structure XIX> wherein

R¹ denotes cyclobutyl, cyclopentyl, cyclohexyl, R-tetrahydrofuran-3-yl, S-tetrahydrofuran-3-yl or tetrahydropyran-4-yl; and X denotes Br or I.

In a further aspect the present invention relates to compounds of the formula XXVI <chemical structure XXVI> wherein

X denotes Br or I; and

Z denotes hydroxy, fluorine, chlorine, bromine, iodine, $C_{1-4}$-alkyl-sulfonyloxy, arylsulfonyloxy, aryl-$C_{1-3}$-alkyl-sulfonyloxy, di-($C_{1-6}$-alkyloxy)-boronyl, di-hydroxy-boronyl, $KF_3B$, $NaF_3B$ or $LiF_3B$; and the term "aryl" is defined as hereinbefore.

In a further aspect the present invention relates to compounds of the formula XXXII <chemical structure XXXII> wherein

R¹ denotes cyclobutyl, cyclopentyl, cyclohexyl, R-tetrahydrofuran-3-yl, S-tetrahydrofuran-3-yl or tetrahydropyran-4-yl; and R² independently of one another denote hydrogen, ($C_{1-18}$-alkyl)carbonyl, ($C_{1-18}$-alkyl)oxycarbonyl, arylcarbonyl, aryl-($C_{1-3}$-alkyl)-carbonyl, aryl-$C_{1-3}$-alkyl, allyl, $R^aR^bR^cSi$, $CR^aR^bOR^c$, wherein two adjacent groups R² may be linked with each other to form a bridging group $SiR^aR^b$, $CR^aR^b$ or $CR^aOR^b$—$CR^aOR^b$;

$R^a$, $R^b$, $R^c$ independently of one another denote $C_{1-4}$-alkyl, aryl or aryl-$C_{1-3}$-alkyl, while the alkyl groups may be mono- or polysubstituted by halogen;

L1 independently of one another are selected from among fluorine, chlorine, bromine, $C_{1-3}$-alkyl, $C_{1-4}$-alkoxy and nitro;

while by the aryl groups mentioned in the definition of the above groups are meant phenyl or naphthyl groups, preferably phenyl groups, which may be mono- or polysubstituted with L1.

DETAILED DESCRIPTION OF THE INVENTION

Unless otherwise stated, the groups, residues and substituents, particularly R¹, R², R³, R', $R^a$, $R^b$, $R^c$, L1, M, X and Z, are defined as above and hereinafter.

If residues, substituents or groups occur several times in a compound, they may have the same or different meanings.

In the processes and compounds according to this invention the following meanings of groups and substituents are preferred:

P R¹ preferably denotes R-tetrahydrofuran-3-yl or S-tetrahydrofuran-3-yl.

R² preferably denotes hydrogen, methylcarbonyl, ethylcarbonyl or trimethylsilyl.

$R^a$, $R^b$, $R^c$ independently of one another preferably denote methyl, ethyl, n-propyl or i-propyl, tert.-butyl or phenyl; most preferably methyl.

R' preferably denotes hydrogen, methyl or ethyl.

In the following the processes according to this invention are described in detail.

The Scheme 0 depicts the conversion of compound II to compound I via removal of the protective groups R² not being hydrogen present in compound II, wherein R¹, R² and R³ are defined as hereinbefore.

Scheme 0:
Synthesis of C-glycoside of formula I via removal of protective groups

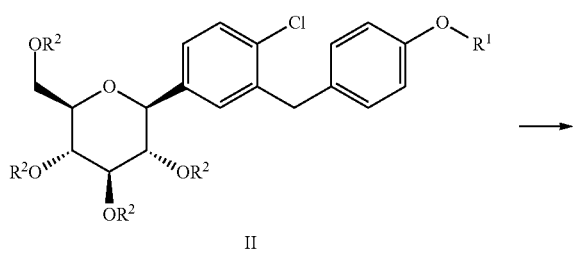

II

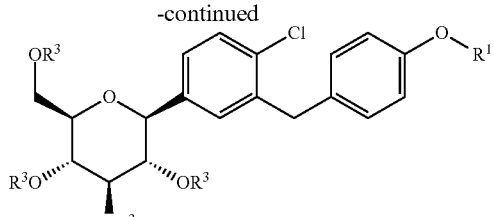

I

Any acyl protecting group R² used is cleaved for example hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C.

A trifluoroacetyl group R² is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Any acetal or ketal protecting group R² used is cleaved for example hydrolytically in an aqueous solvent or aqueous mixture of solvents, e.g. in water, isopropanol/water, acetic acid/water, tetrahydrofuran/water or dioxane/water, in the presence of an acid such as trifluoroacetic acid, hydrochloric acid or sulphuric acid or aprotically, e.g. in the presence of iodotrimethylsilane, at temperatures between 0 and 120° C., preferably at temperatures between 10 and 100° C.

A silyl group R², for example trimethylsilyl, is cleaved for example in water, an aqueous solvent mixture or a lower alcohol such as methanol or ethanol in the presence of a base such as lithium hydroxide, sodium hydroxide, potassium carbonate or sodium methoxide.

In aqueous or alcoholic solvents, acids such as e.g. hydrochloric acid, trifluoroacetic acid or acetic acid are also suitable. For cleaving in organic solvents, such as for example diethyl ether, tetrahydrofuran or dichloromethane, it is also suitable to use fluoride reagents, such as e.g. tetrabutylammonium fluoride.

A benzyl, methoxybenzyl or benzyloxycarbonyl group R² is advantageously cleaved hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group R² is preferably cleaved by treating with an acid such as trifluoroacetic acid or hydrochloric acid or by treating with iodotrimethylsilane optionally using a solvent such as methylene chloride, dioxane, methanol or diethylether.

The glucose derivatives of formula II may be synthesized via reduction of the anomeric carbon-oxygen bond of compound III (Scheme 1).

Scheme 1: Reduction of the compound III

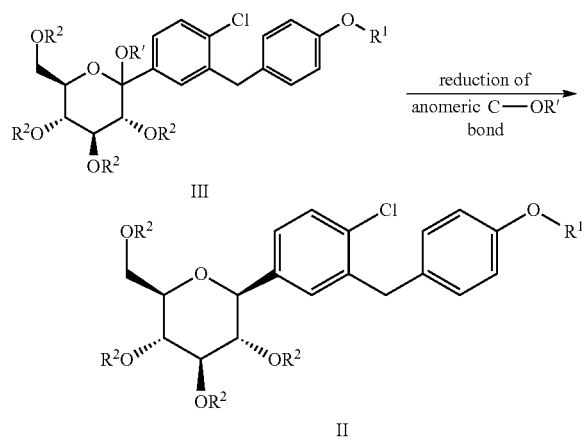

R' and R$^1$ are defined as hereinbefore. R$^2$ is defined as hereinbefore and represents for example hydrogen, acetyl, pivaloyl, benzoyl, tert-butoxycarbonyl, benzyloxycarbonyl, trialkylsilyl, benzyl or substituted benzyl. In case two adjacent groups R$^2$ are linked with each other to form a bridging group they preferably form an acetal such as e.g. benzylideneacetal, a ketal such as e.g. isopropylideneketal, or an ethylene group that results in the formation of a dioxane such as e.g. the combination with 2,3-dimethoxy-butylene which is linked via position 2 and 3 of the butylene group to the oxygen atoms of the pyranose. A preferred meaning of R$^2$ is hydrogen or tri-($C_{1-3}$-alkyl)silyl, such as trimethylsilyl or triisopropylsilyl. R' preferably denotes hydrogen or $C_{1-4}$-alkyl, in particular methyl or ethyl.

The reduction may be conducted with a reducing agent in the presence of or without a Lewis acid. Suitable reducing agents include for example silanes such as e.g. triethylsilane, tripropylsilane, triisopropylsilane, or diphenylsilane, sodium borohydride, sodium cyanoborohydride, zinc borohydride, borane complexes, lithium aluminum hydride, diisobutylaluminum hydride, or samarium iodide. Suitable Lewis acids are such as e.g. boron trifluoride etherate, trimethylsilyl triflate, titanium tetrachloride, tin tetrachloride, scandium triflate, copper(II) triflate, or zinc iodide; or suitable Lewis acids are Brønsted acids such as e.g. hydrochloric acid, toluenesulfonic acid, trifluoroacetic acid, or acetic acid. Depending on the reducing agent the reductions may be carried out without a Lewis acid. The reaction may be carried out in a solvent such as for example methylene chloride, chloroform, acetonitrile, toluene, hexane, diethylether, tetrahydrofuran, dioxane, ethanol, water, or mixtures thereof. The solvent is preferably selected in view of the reducing agent and the optional Lewis acid. Preferred reaction temperatures are between −80° C. and 120° C., more preferably between −30 and 80° C.

One particularly suitable combination of reagents consists for example of triethylsilane and boron trifluoride etherate, which is conveniently used in acetonitrile, dichloromethane, or mixtures thereof at temperatures from −60° C. to 60° C.

The reduction is preferably carried out in the absence of water, in particular with a content of water in the reaction mixture below 2000 ppm, even more preferably below 1000 ppm.

In addition to the reducing agents mentioned above, hydrogen may be used for the reduction intended. This transformation may be accomplished in the presence of a transition metal catalyst such as e.g. palladium on charcoal, palladium oxide, platinum oxide, or Raney nickel, in solvents such as e.g. tetrahydrofuran, ethyl acetate, methanol, ethanol, water, or acetic acid at temperatures of −40° C. to 100° C. and at hydrogen pressures of 1 to 10 Torr.

The glucose derivatives of formula III may be synthesized from D-gluconolactone or a derivative thereof by reacting the desired benzylbenzene compound in the form of an organometallic compound (Scheme 2a).

Scheme 2a: Addition of an Organometallic Compound to Gluconolactone

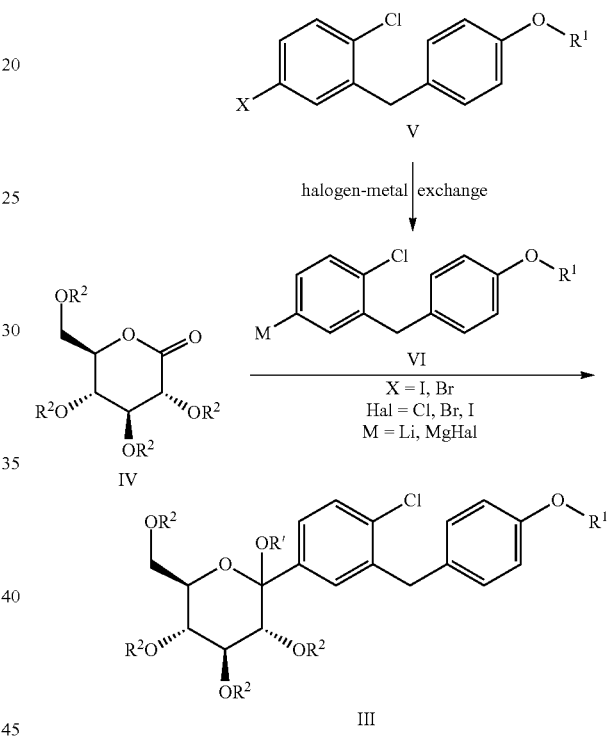

The Scheme 2a and the following sections describe preferred conditions and embodiments of the process according to the third aspect of this invention.

The Grignard or Lithium reagent of benzylbenzene (VI) may be prepared from the corresponding brominated or iodinated benzylbenzene V either via a so-called halogen-metal exchange reaction or by inserting the metal into the carbon-halogen bond. The halogen-metal exchange to synthesize the corresponding lithium compound VI may be carried out for example with an organolithium compound such as e.g. n-, sec- or tert-butyllithium. A preferred amount of the organolithium compound is in the range from about 1 to 2 mol, more preferably about equimolar with respect to the benzylbenzene V.

The analogous magnesium compound may also be generated by a halogen-metal exchange with a suitable Grignard reagent such as $C_{3-4}$-alkylmagnesium chloride or bromide, for example isopropyl- or sec-butylmagnesium bromide or chloride or diisopropyl- or di-sec-butylmagnesium without or in the presence of an additional salt such as e.g. lithium chloride that may accelerate the metalation process. The specific transmetalating organomagnesium compound may also be generated in situ from suitable precursors (see e.g. *Angew. Chem.* 2004, 116, 3396-3399 and *Angew. Chem.* 2006, 118, 165-169 and references quoted therein). The Grignard reagent is preferably used in an amount in the range from about 1 to 5 mol per mol of the benzylbenzene V.

The halogen-metal exchange reactions are preferably carried out between −100° C. and 40° C., particularly preferably between −80° C. and 10° C. A more preferred temperature range in the halogen-lithium exchange reaction is −80° C. and −15° C.

Preferably the halogen-metal exchange reaction is carried out in an inert solvent or mixtures thereof, such as for example diethylether, dioxane, tetrahydrofuran, diethylene glycol dimethyl ether, toluene, hexane, dimethylsulfoxide, dichloromethane or mixtures thereof. Particularly preferred solvents are selected form among tetrahydrofuran, diethylene glycol dimethyl ether, hexane and mixtures thereof.

The magnesium or lithium derivatized compounds thus obtained may optionally be transmetalated with metal salts such as e.g. cerium trichloride, zinc chloride or bromide, indium chloride or bromide, to form alternative organometal compounds (VI) suitable for addition.

Alternatively, the organometal compound VI may also be prepared by inserting a metal into the carbon-halogen bond of the haloaromatic compound V. Lithium or magnesium are suitable elemental metals for this transformation. The insertion can be achieved in solvents such as e.g. diethylether, dioxane, tetrahydrofuran, toluene, hexane, dimethylsulfoxide and mixtures thereof at temperatures ranging from −80 to 100° C., preferably at −70 to 40° C. In cases in which no spontaneous reaction takes place prior activation of the metal might be necessary such as e.g. the treatment with 1,2-dibromoethane, iodine, trimethylsilylchloride, acetic acid, hydrochloric acid and/or sonication.

The addition of the organometal compound VI to gluconolactone or derivatives thereof (IV) is preferably carried out at temperatures between −100° C. and 40° C., particularly preferably at −80 to −10° C., in an inert solvent or mixtures thereof, to obtain the compound of formula III. In case the compound VI is a lithiumorganic compound the addition is even more preferably carried out at temperatures in the range from −80 to −20° C. In case the compound VI is a magnesiumorganic compound particularly preferred temperatures during the addition are in the range from −30° C. to −15° C.

All foregoing reactions may be performed in air though the execution under inert gas atmosphere is preferred. Argon and nitrogen are preferred inert gases.

The metalation and/or coupling reaction may also be carried out in microreactors and/or micromixers which enable high exchange rates; for example analogously to the processes described in WO 2004/076470.

Suitable solvents for the addition of the metalated compound VI to the appropriately protected gluconolactone IV are e.g. diethylether, toluene, methylene chloride, hexane, tetrahydrofuran, dioxane, N-methylpyrrolidone and mixtures thereof.

The addition reactions may be carried out without any further adjuvants or in the presence of a promoter such as e.g. $BF_3 \cdot OEt_2$ or $Me_3SiCl$ which may be advantageous in the case of sluggishly reacting coupling partners (see M. Schlosser, Organometallics in Synthesis, John Wiley & Sons, Chichester/New York/Brisbane/Toronto/Singapore, 1994).

Preferred definitions of the substituents $R^2$ in Scheme 2a are benzyl, substituted benzyl, trialkylsilyl, particularly preferably tri-($C_{1-3}$-alkyl)silyl, such as trimethylsilyl, triisopropylsilyl, 4-methoxybenzyl and benzyl. If two adjacent substituents $R^2$ are linked together, these two substituents are preferably part of a benzylideneacetal, 4-methoxybenzylideneacetal, isopropylketal or constitute a dioxane with 2,3-dimethoxy-butylene which is linked via the 2 and 3 positions of the butane with the adjacent oxygen atoms of the pyranose. The group R' preferably denotes hydrogen, $C_{1-4}$-alkyl, $C_{1-4}$-alkylcarbonyl or $C_{1-4}$-alkyloxycarbonyl, particularly preferably hydrogen, methyl or ethyl.

The group R' is introduced after the addition of the organometallic compound VI or a derivative thereof to the gluconolactone IV. If R' equals hydrogen or $C_{1-4}$-alkyl the reaction solution is treated with an alcohol, in particular an $C_{1-4}$-alkanol, such as e.g. methanol or ethanol or water in the presence of an acid such as e.g. acetic acid, methanesulfonic acid, toluenesulfonic acid, sulfuric acid, trifluoroacetic acid, or hydrochloric acid. This reaction with the alcohol or water is preferably carried out at temperatures in the range from about 0° C. to 80° C., particularly from about 20° C. to 60° C. During installing R' the protective groups $R^2$ may be cleaved if labile under the reaction conditions employed resulting in the corresponding protonated compound, i.e. compound III in which $R^2$ equals H. For example protecting groups wherein $R^2$ denotes trialkylsilyl, such as trimethylsilyl, are usually cleaved when the reaction solution is treated with an alcohol and/or water in the presence of an acid so that a compound III is obtained wherein $R^2$ denotes H.

R' may also be attached after preparation of the hydrogen compound III (R'=H) by reacting the anomeric hydroxyl group with a suitable electrophile such as e.g. methyl iodide, dimethyl sulfate, ethyl iodide, diethyl sulfate, acetyl chloride, or acetic anhydride in the presence of a base such as e.g. triethlyamine, ethyldiisopropylamine, sodium or potassium or cesium carbonate, sodium or potassium or cesium hydroxide. The hydroxyl group can also be deprotonated prior to the addition of the electrophile with e.g. sodium hydride.

Scheme 2b: Synthesis of C-Glucosides - Approach 2

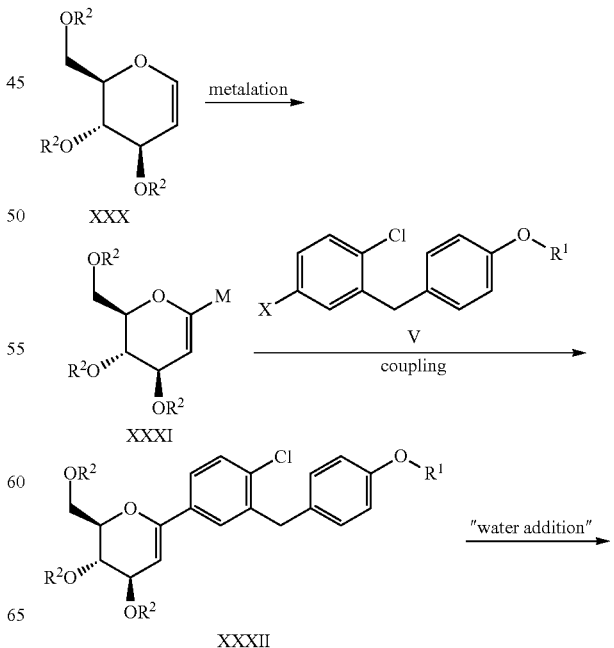

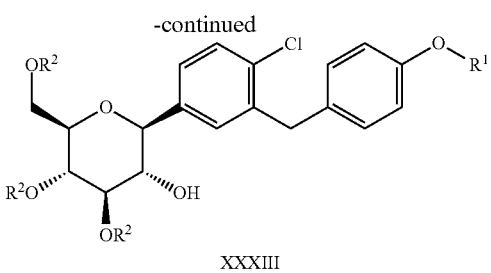

XXXIII

Approach 2 depicted in Scheme 2b illustrates the synthesis of the C-glucosides commencing with an appropriately protected D-glucal XXX (see *Synlett* 2004, pp. 1235-1238; *Org. Lett.* 2003, 5, pp. 405-2408 and references quoted therein for analogous approaches). The protected D-glucal XXX is metallated to yield the D-glucal derivative XXXI wherein M denotes a lithium, magnesium, zinc, indium, boron, tin, silicon or chromium moiety; in particular lithium, magnesium halide, zinc halide, indium halide, boronic acid, boronic acid ester.

Metalation of glucal XXX at C-1 may be accomplished by deprotonation with a strong base. Strong bases capable of deprotonating the glucal may be lithium bases such as e.g. n-butyl lithium, sec-butyl lithium or tert-butyl lithium. The C-1 lithiated glucal thus obtained may be transmetalated with different electrophilic metal sources delivering the corresponding C-1 metalated glucal derivative. Metal species suitable for the subsequent transformation, coupling with the aglycon moiety, are derived from e.g. lithium, magnesium, zinc, indium, boron, tin, silicon, and chromium. The transmetalation of the glucal compound from lithium to one of the metals mentioned may be conducted with the corresponding e.g. halides such as chloride, bromide and iodide, sulfonates such as e.g. trifluoromethanesulfonate, and alcoxides such as e.g. methoxide, ethoxide, propoxide and isopropoxide of the metal species to be introduced. Depending on the metal transmetalated to the metal may bear more than one glucal residue such as in the corresponding triglucal indium or diglucal zinc. The corresponding monoglucal substituted metal derivatives are employable as well. The metalation of glucal with a strong base, in particular a lithium base, is preferably performed in inert solvents such as e.g. tetrahydrofuran, ether, dioxane, dimethoxyethane, hexane, and toluene. Preferred temperatures are in the range between –80° C. and 50° C. The transmetalation may be conducted in the same solvents depending on the electrophilic metal species in the same temperature range. Among the electrophilic metal species usable in the transmetalation the following are among the most appropriate: trialkylchlorostannane, tetrachlorostannane, trialkylchlorosilane, trialkoxychlorosilyl chloride or bromide, boron trichloride, trialkyl borates, dialkylchloroborane, indium trichloride, zinc chloride, triflate or bromide, magnesium chloride or bromide. This compilation is by no means meant to restrict the employable metal electrophiles to the ones mentioned but is supposed to give an idea of electrophiles that can be used. In the above and below described reactions the protecting groups $R^2$ are preferably chosen in view of their stability under basic conditions, in particular the groups $R^2$ independently of each other denote —$SiR^aR^bR^c$, wherein two adjacent groups $R^2$ may be linked with each other to form a bridging group $SiR^aR^b$, wherein $R^a$, $R^b$, $R^c$ are defined as hereinbefore, preferably denote isopropyl.

The metalated glucal derivative of the formula XXXI thus obtained may be coupled with the agylcon V wherein the group X denotes a leaving group, preferably selected from the group consisting of chlorine, bromine, iodine, sulfonate such as e.g. trifluoromethane-sulfonate, tosylate, benezene-sulfonate, and mesylate, chlorosulfonate, sulfonic acid or salts thereof, hydroxycarbonyl or salts thereof, nitrile, and diazonium salts. The coupling reactions are preferably carried out in the presence of a transition metal catalyst such as e.g. salts, complexes or elemental modifications of palladium, copper, iron, and nickel. Complexes can be formed in situ or prior to the addition of the transition metal to the reaction mixture. The ligands in the complexes of the transition metal may be e.g. triarylphosphine, aryldialkyl-phosphine, trialkylphosphine, phosphite, 1,3-disubstituted dihydroimidazolium carbene, 1,3-disubstituted imidazolium carbene, and alkenes. The reaction is preferably carried out in an inert organic solvent or mixtures thereof. Suitable solvents may be e.g. tetrahydrofuran, dioxane, dimethoxyethane, hexane, toluene, benzene, dimethylformamide, dimethylacetamide, N-methylpyrrolidinone, acetone, ethyl acetate, water, methanol, ethanol, propanol, isopropanol, ethylene glycol, polyethylene glycol. The coupling reactions are preferably carried out between –80° C. and 180° C., more preferably at –20° C. to 120° C. The concluding synthetic step in Scheme 2b is the formal addition of water to the double bond in the glucal moiety. This process may be done by e.g. hydroboration that results in the formation of the 2-boron-2-desoxy glucose derivative that can be converted to the corresponding glucose compound by oxidation of the carbon-boron bond. Suitable boranes for the hydroboration are e.g. borane or ether, thioether or amine adducts thereof, alkylboranes or dialkylboranes such as e.g. hexylborane, thexylborane, diethylborane and 9-BBN, pinacolborane, catecholborane, halo or dihaloborane such as e.g. dichloroborane. The hydroboration may be conducted in e.g. tetrahydrofuran, hexane, cyclohexane, ether, toluene, benzene, dichloromethane. A preferred temperature range is between –50° C. and 150° C., preferably between –20° C. and 50° C. The oxidative cleavage of the carbon-boron bond may be performed with an oxidizing reagent such as e.g. hydrogen peroxide, tert-butyl hydrogen peroxide, sodium perborate, and trialkylamine N-oxide. Depending on the oxidizing reagent the reaction is advantageously carried out in the presence of a base such as e.g. sodium hydroxide. The reaction is preferably carried out in an inert organic solvent or mixtures thereof. Preferred solvents are selected from among tetrahydrofuran, water, alcohols, dioxane, diemethoxyethane, cyclohexane, hexane, toluene, dichloromethane and mixtures thereof. A preferred temperature range is between –30 to 150° C., preferably between 0 to 110° C. An alternative to the hydroboration in order to add water to the double bond is the combination of epoxidation or dihydroxylation of the double bond and reduction of the resultant anomeric carbon-oxygen bond. Suitable oxidizing reagents for the epoxidation are e.g. dimethyldioxirane, trifluordimethyldioxirane, 3-chloroperoxybenzoic acid, hydrogen peroxide and oxygen in the presence of a transition metal catalyst. Another suitable oxidizing agent is peroxomonosulfuric acid, peroxodisulfuric acid and salts thereof, in the presence of at least one ketone, in particular triple salts of the formula 2 $KHSO_5 \times KHSO_4 \times K_2SO_4$ which are commercially available, for example under the brand names OXONE® (trademark E.I. du Pont de Nemours) and CAROAT® (trademark Degussa, Peroxid-Chemie GmbH & Co. KG, Dr.-Gustav-Adolph-Str. 3, D-82049 Pullach, Germany) in combination with a ketone, preferably acetone. Dihydroxylation can be accomplished with e.g. osmium tetroxide and dipotassium osmium tetroxide preferably in the presence of a co-oxidant such as e.g. potassium hexacyano-ferrate, hydrogenperoxide, and N-methylmorpholine N-oxide; hydrolytic opening of the oxirane resulting from the epoxidation gives also access to the dihydroxylation product. The oxidations may be conducted in inert organic solvents or mixtures thereof such as e.g. dichloromethane, tetrahydrofuran, ether, hexane, cyclohexane, dioxane, acetone, ethyl acetate, acetonitrile, water, alcohols and mixtures thereof. A preferred temperature range is between −80° C. and 100° C., preferably between −50° C. and 50° C. Reduction of the anomeric carbon-oxygen bond of the oxirane or dihydroxylation product may be accomplished with reducing agents such as e.g. trialkylsilanes such as e.g. triethylsilane, borohydrides such as e.g. sodium borohydride and aluminum hydrides such as e.g. diisobutylaluminum hydride. Depending on the reducing agent the presence of a Lewis acid such as e.g. boron trifluoride etherate, zinc chlorides, trimethylsilyl chloride or triflate, alkyl-, dialkyl- or aluminum halide, copper triflate, and Brønsted acids such as e.g. hydrochloric acid, acetic acid, alkyl- or arylsulfonic acids, trifluoroacetic acid is necessary or at least advantageous. Dichloromethane, acetonitrile, tetrahydrofuran, ether, hexane are among the preferred solvents. A preferred temperature range is between −80° C. and 120° C. Hydrogen in combination with a transition metal catalyst such as e.g. palladium on carbon, Raney-nickel, and palladium hydroxide may be used as well.

Subsequently, the product of the formula XXXIII may be transferred into the product of the formula I by cleaving, in particular hydrolysing, the protective groups $R^2$ not being hydrogen, advantageously employing methods as described hereinbefore.

Scheme 2c: Synthesis of C-Glucosides - Approach 3

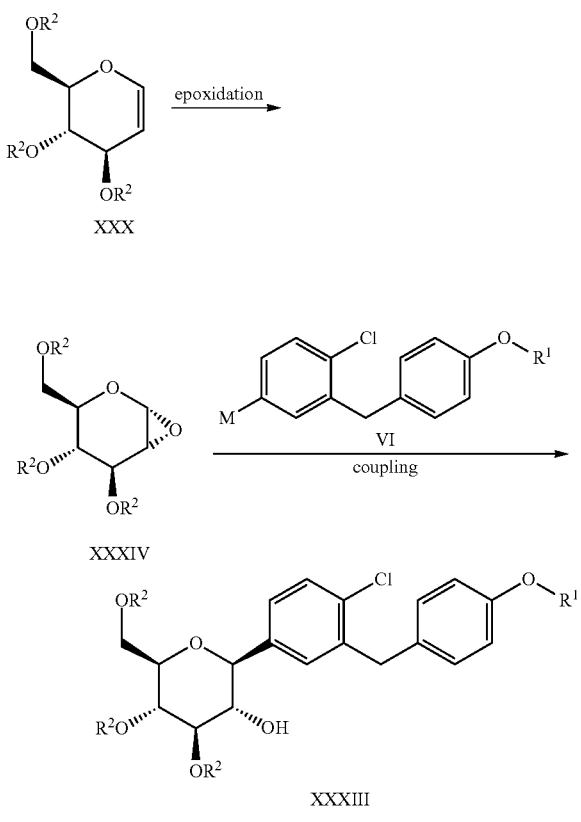

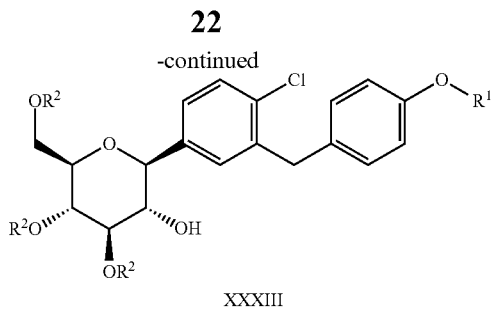

XXXIII

Scheme 2c illustrates an alternative access to C-glucosides starting from the glucal XXX (see e.g. Synlett 2003, pp. 870-872; Tetrahedron 2002, 58, pp. 1997-2009 and references quoted therein for analogous approaches). Epoxidation with an appropriate oxidizing reagent transforms the glucal XXX into the corresponding glucaloxide XXXIV. Suitable reaction conditions for this transformation have already been described for the analogous conversion of glucal XXXII shown in Scheme 2b. Among the oxidizing agents described there dimethyldioxirane and trifluorodimethyldioxirane generated separately or in situ are preferred. Said oxidizing agents may be obtained with e.g. peroxomonosulfuric acid, peroxodisulfuric acid and salts thereof, in the presence of at least one ketone, in particular with triple salts of the formula 2 $KHSO_5 \times KHSO_4 \times K_2SO_4$ which are commercially available, for example under the brand names OXONE® (trademark E.I. du Pont de Nemours) and CAROAT® (trademark Degussa, Peroxid-Chemie GmbH & Co. KG, Dr.-Gustav-Adolph-Str. 3, D-82049 Pullach, Germany) in combination with a ketone, preferably acetone. The reaction is preferably carried out at temperatures in the range between −80 and 0° C. in an inert organic solvent or mixtures thereof. Preferred solvents are selected from the group consisting of dioxan, 1,2-dimethoxyethane, toluene, hexane, tetrahydrofuran, diethylether, dichloromethane and mixtures thereof. In the above and below described reactions the protecting groups $R^2$ are preferably independently of each other selected from the group consisting of $C_{1-4}$-alkylcarbonyl, $C_{1-4}$-alkyloxycarbonyl, arylmethyl and $R^aR^bR^cSi$, wherein aryl, $R^a$, $R^b$ and $R^c$ are defined as hereinbefore.

The ensuing reaction, epoxide opening with a metalated aglycon of the formula VI in which M denotes a lithium, magnesium, zinc, indium, aluminum or boron moiety, affords the desired C-glucoside. For this transformation the preferred meaning of M is lithium, magnesium halide, zinc halide, indium halide, aluminum halide, dialkylaluminum halide or boronic acid compound. The synthesis of the lithium or magnesium derivative of compound VI has been detailed in Scheme 2a, whereas the transmetalation of these compounds to one of the alternative metal species may be done in analogy to the transmetalation of the lithiated glucal to the same metal derivatives presented in Scheme 2b. The epoxide opening reaction may take place without an adjuvant or in the presence of a transition metal salt or complex such as e.g. copper cyanide or halide or in the presence of a Lewis acid such as e.g. borontrifluoride etherate or trimethylsilyl-chloride or triflate. Suitable inert solvents may be e.g. acetone, ether, tetrahydrofuran, acetonitrile, dichloromethane, toluene, hexane and mixtures thereof. A preferred temperature range is between −80° C. to 60° C.

Subsequently the product of the formula XXXIII may be transferred into the product of the formula I by cleaving, in particular hydrolysing, the protective groups $R^2$ not being hydrogen, advantageously employing methods as described hereinbefore.

Scheme 2d: Synthesis of C-Glucoside - Approach 4

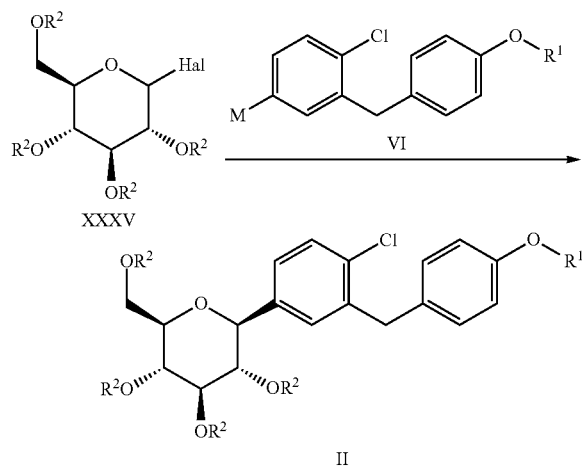

Hal = F, Cl, Br, OAc, OAlk

Hal = F, Cl, Br, OAc, OAlk

A glucose derivative XXXV bearing a potential leaving group Hal at the anomeric carbon may be utilized as starting material for the coupling with a metalated aryl aglycon VI as well (see *J. Carbohydr. Chem.* 1994, 13, pp. 303-321 and references quoted therein for analogous approaches). Suitable leaving groups Hal may be halides, alcoxides, acyl groups such as carboxylates and carbonates; in particular F, Cl, Br, $C_{1-3}$-alkylcarbonyloxy, $C_{1-3}$-alkyloxy-carbonyloxy or $C_{1-3}$-alkyloxy, such as e.g. Cl, Br, methoxide, acetate and methylcarbonate. Suitable metals M attached to the aryl part are e.g. lithium, magnesium as e.g. magnesium halide, zinc as e.g. zinc halide, indium as e.g. indium dihalide, boron as e.g. boronic acid or boronic acid ester. The preparation of these metalated aryl compounds from the corresponding halogenated aromats has been described in Scheme 2c. The substitution reactions can be run without or in the presence of an additional Lewis acid such as e.g. boron trifluoride etherate, trimethylsilyl chloride or triflate depending on the metal species and glucosyl donor employed. The reaction is preferably carried out in an inert organic solvents or mixtures thereof. The preferred solvent is preferably chosen in view of the metalated aglycon, glucosyl donor and adjuvants needed; the following solvents may be advantageous: tetrahydrofuran, dioxane, toluene, hexane, ether, N-methylpyrrolidinone, dimethylacetamide, dimethylformamide, acetonitrile, dichloromethane and mixtures thereof. The coupling reaction is usually conducted between −80° C. and 120° C., preferably at −60° C. to 60° C. In the above and below described reactions the protecting groups $R^2$ are preferably independently of each other selected from the group consisting of $C_{1-4}$-alkylcarbonyl, $C_{1-4}$-alkyloxycarbonyl, arylmethyl and $R^a R^b R^c Si$, wherein aryl, $R^a$, $R^b$ and $R^c$ are defined as hereinbefore.

Subsequently the product of the formula II may be transferred into the product of the formula I by cleaving, in particular hydrolysing, the protective groups $R^2$ not being hydrogen, advantageously employing methods as described hereinbefore.

The synthesis of haloaromatic compound V may be carried out using standard transformations in organic chemistry or at least methods known from the specialist literature in organic synthesis (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein). The synthesis strategies described in the following provide a demonstration of this, by way of example.

In the following schemes
X denotes bromine or iodine,
Alk denotes $C_{1-4}$-alkyl,
R denotes $C_{1-4}$-alkyl, $C_{1-4}$-alkoxy, $CF_3$, aryl or aryl-$C_{1-3}$-alkyl, wherein aryl-groups may be mono- or polysubstituted with L1;
P $R^1$ is as defined hereinbefore; and
L1 is as defined hereinbefore;
unless indicated otherwise.

Scheme 3 displays the synthesis of aglycon V starting from benzophenone derivative IX that can be prepared from a benzoic acid derivative and a phenylalkylether or a metalated phenylalkylether (see Schemes 5, 8, and 9). The first step is the cleavage of the ether moiety in compound IX that can be accomplished under neutral, acidic and basic conditions. Suitable acidic reagents for this transformation are e.g. boron trichloride or tribromide or triiodide, trimethylsilyl iodide, aluminum chloride or bromide, hydrobromic acid, hydrochloric acid, cerium chloride, trifluoroacetic acid, and trifluoromethylsulfonic acid that may be used in concert with a nucleophile such as e.g. metal halides such as e.g. sodium iodide, water, alkylthiols, thioanisole, and dialkylsulfides, that may scavenge the departing alkyl group. Depending on the acid used solvents selected from the group consisting of halogenated hydrocarbons, such as e.g. dichloromethane, chloroform or 1,2-dichloroethane, acetonitrile, toluene, hexane, acetic acid and combinations thereof are preferred. Reactions without additional solvent are also feasible. The reactions are generally carried out at −90 to 150° C., preferably at −80 to 50° C. Cleavage under neutral or basic conditions can be done e.g. with metal thiolates such as e.g. sodium sulfide, sodium ethanethiolate, sodium trimethylsilyl-thiolate, potassium thiophenolate, sodium cyanide, and lithium iodide in solvents such as e.g. dimethylformamide, dimethylacetamide, 1,3-dimethyl-2-oxohexahydropyrimidine, N-methylpyrrolidone, tetrahydrofuran, collidine, and quinoline at temperatures between 0 and 250° C., preferably at 50 to 180° C. The second step outlined in Scheme 3 comprises the attachment of residue $R^1$ to the phenolic oxygen of compound VIII. This transformation can be carried out under basic conditions as classical nucleophilic substitution reaction. Accordingly, the phenol is deprotonated by a base to from the corresponding phenolate. Suitable bases are e.g. group I or II metal salts, in particular carbonates, hydroxides, alkoholates such as e.g. methoxide, ethoxide or tertbutoxide, and metal hydrides such as e.g. sodium hydride. The reaction can be conducted in polar and non-polar solvents as well as without solvent, preferably in alcohols such as e.g. ethanol, isopropanol or butanol, acetone, water, dimethylformamide, dimethylacetamide, N-methylpyrollidone, dimethylsulfoxide, tetrahydrofuran, dichloromethane and mixtures thereof. The phenolate obtained then is reacted with an electrophile of $R^1$ at temperatures between 20 and 180° C., preferably between 40 and 120° C. Suitable electrophiles of $R^1$ are e.g. halides, such as chlorides, bromides or iodides, alkylsulfonates such as e.g. methylsulfonate, trifluoromethanesulfonate, arylsulfonates such as e.g. 4-bromophenylsulfonate, 4-methylphenylsulfonate or phenylsulfonate. An alternative approach to attach $R^1$ to the phenol VIII is the addition of the phenol VIII to a group $R^1$ that bears an appropriately situated C═C double bond. This reaction may be conducted in the presence of a Brønsted acid such as e.g. trifluoro-methanesulfonic acid, hydrochloric acid, sulfuric acid, or a transition metal catalysts such as e.g. platinum, ruthenium, palladium, or gold salts or complexes thereof; preferred salts are triflate, chloride, bromide and iodide (see e.g. Cai-Guang Yang and Chuang He; *J. Am. Chem. Soc.* 2005, 127, and references quoted therein). The solvent most appropriate for the addition depends on the acid or transition metal that is employed. Solvents such as e.g. toluene, benzene, dichloromethane, 1,2-dichloroethane, acetonitrile, tetrahydrofuran, dimethylacetamide, N-methylpyrrolidone, hexane, and ethyl acetate may be suited. The reaction is carried out at 0 to 200° C., preferably at 20 to 140° C. Scheme 3 concludes with the reduction of benzophenone VII to furnish aglycon V. Proper reducing agents for this conversion are e.g. silane such as e.g. Et$_3$SiH and triisopropylsilane, borohydride such as e.g. NaBH$_4$, and aluminum hydride such as e.g. LiAlH$_4$ in the presence of a Lewis acid such as for example BF$_3$*OEt$_2$, tris(pentafluorophenyl)borane, trifluoroacetic acid, hydrochloric acid, aluminum chloride, or InCl$_3$. The reactions are preferably carried out in solvents such as e.g. halogenated hydrocarbons such as dichloromethane and 1,2-dichloroethane, toluene, benzene, hexane, acetonitrile and mixtures thereof at temperatures of −30 to 150° C., preferably at 20 to 100° C. Reductions with hydrogen in the presence of a transition metal catalyst such as e.g. Pd on charcoal are another possible method of synthesis but might be less suited here due to competing reduction processes in the rest of the molecule. Reductions according to Wolff-Kishner or variants thereof are also conceivable. Hence, the ketone is converted with hydrazine or a derivative thereof such as e.g. 1,2-bis(tert-butyldimethylsilyl)hydrazine into the hydrazone which breaks down under strongly basic reaction conditions and heating to liberate the diphenylmethane V and nitrogen. The reaction may be carried out in one pot or after isolation of the hydrazone or a derivative thereof in two separate reaction steps. Suitable bases include e.g. KOH, NaOH or KOtBu in solvents such as e.g. ethyleneglycol, toluene, DMSO, 2-(2-butoxyethoxy)ethanol or tert-butanol; solvent-free reactions are also possible. The reactions may be performed at temperatures between 20 and 250° C., preferably between 80 and 200° C. An alternative to the basic conditions of the Wolff-Kishner reduction is the Clemmensen reduction which takes place under acidic conditions, which may also be used here if no concurrent dehalogenation occurs.

Scheme 3: Synthesis of Aglycon V - Approach 1

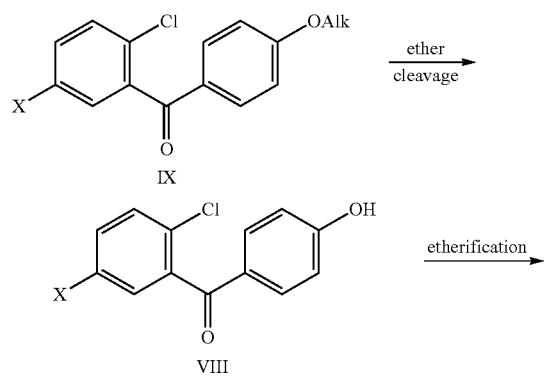

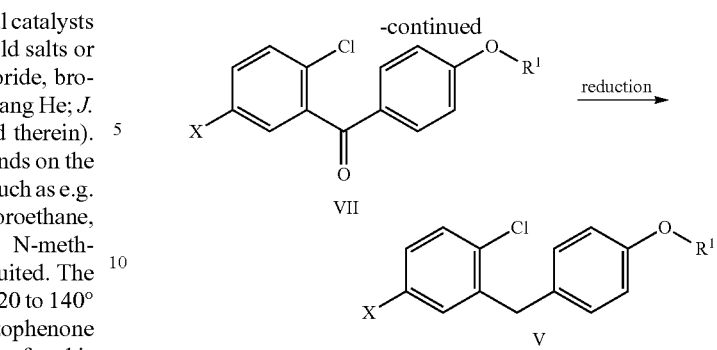

Scheme 4 outlines a slightly different approach to the synthesis of aglycon V compared with Scheme 3. Nevertheless, the ether cleavage and the ensuing etherification delineated in Scheme 4 can principally be carried out under reaction conditions analogous to the synthesis described above with respect to the compounds VIII and VII.

Scheme 4: Synthesis of Aglycon V - Approach 2

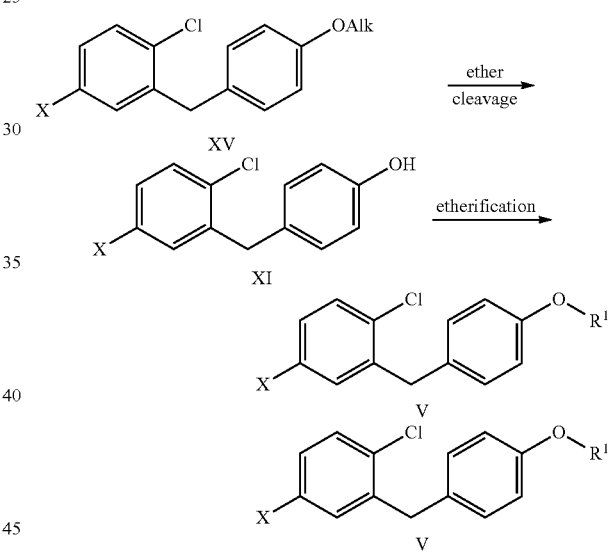

Scheme 5 describes the assembly of aglycon V starting from the known benzoyl chloride XII and phenylether derivative XIII. The first step, the preparation of benzophenone VII, can be characterized as Friedel-Crafts or Friedel-Crafts-type acylation, a well-known and widely used method in organic synthesis. In principal, the benzoyl chloride XII may be replaced by other benzoic acid derivatives such as e.g. benzoyl anhydrides, esters, or benzonitriles. This classic reaction has a wide substrate scope and is commonly carried out in the presence of a catalyst such as e.g. AlCl$_3$, FeCl$_3$, iodine, iron, ZnCl$_2$, sulfuric acid, or trifluoromethanesulfonic acid which is used in catalytic or stoichiometric amounts. The reactions are preferentially performed in chlorinated hydrocarbons such as e.g. dichloromethane or 1,2-dichloroethane, in hydrocarbons such as e.g. hexane at temperatures ranging from −30 to 140° C., preferably at 30 to 100° C. However, other solvents and solvent mixtures and also solvent-free reactions or reactions in a microwave oven are also possible. The second reaction step in Scheme 5 is analogous to the final reaction in Scheme 3 as described hereinbefore.

Scheme 5: Synthesis of Aglycon V - Approach 3

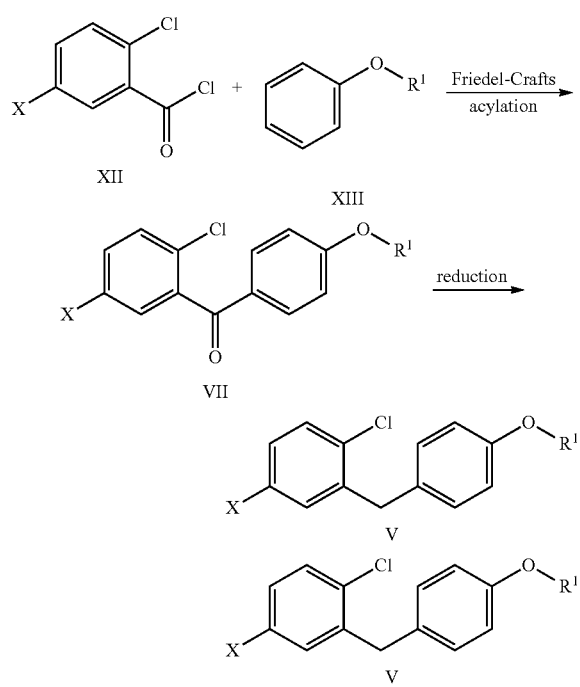

Scheme 6 illustrates an alternative synthesis of the aglycon V via a Friedel-Crafts-type alkylation of phenylether XIII with benzyl electrophile XIV (see *Angew. Chem.* 2005, 117, pp. 242-246 and *Syn. Commun.* 2004, 34, pp. 3161-3165 and references quoted therein). The reaction is commonly conducted in the presence of a catalyst, in particular of a Lewis acid such as e.g. scandium chloride, zinc chloride, aluminium chloride or boron trifluoride, of a Brønsted acid such as e.g. sulfuric acid, hydrochloric acid or hydrogenfluoride, of a lanthanide salt such as e.g. cerium sulfate or ytterbium chloride, of an actinide salt, of a transition metal salt or of a complex such as e.g. $IrCl_3*nH_2O$, $RhCl_3*nH_2O$, $H_2[PtCl_6]*6H_2O$ or $H_2[PdCl_6]*6H_2O$. The catalysts can be applied in stoichiometric or excess quantities though in many cases substoichometric or even catalytic amounts are sufficient. The reactions are usually carried out with an excess of aromatic compound XIII relating to the benzyl electrophile without solvent; though inert solvents such as e.g. halogenated hydrocarbons or hydrocarbons can be employed as well. The reaction is generally conducted at temperatures between 0 and 200° C., preferably at 20 to 140° C.

Scheme 6: Synthesis of Aglycon V - Approach 4

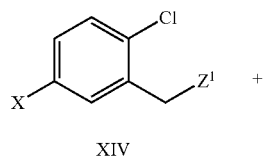

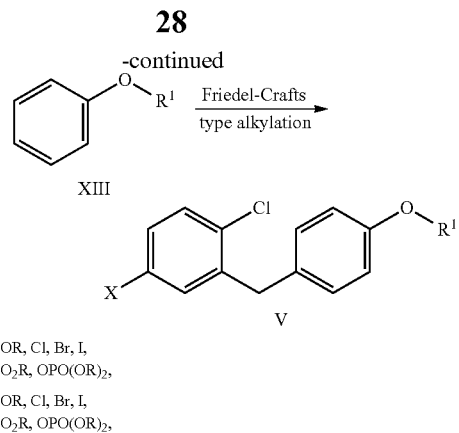

$Z^1$ = OH, OR, OCOR, Cl, Br, I, OCOOR, OSO$_2$R, OPO(OR)$_2$, $Z^1$ = OH, OR, OCOR, Cl, Br, I, OCOOR, OSO$_2$R, OPO(OR)$_2$,

The approach presented in Scheme 7 starts with the synthesis of phenylether XVI from monosubstituted phenol XV that can be conducted analogously to the synthesis of the etherification shown in Scheme 3. In the second step of Scheme 7 the residue $Z^2$ is exchanged for a metal or substituted metal residue. Lithium or magnesium substituted aromatic compounds XVII may be prepared from chlorinated, brominated, or iodinated aromatic compounds XV in the same manner as for the metalated aglycon VI described in Scheme 2a. The corresponding boron substituted compound such as e.g. boronic acid, boronic acid ester, or dialkylarylborane is accessible from these metalated phenyl groups XVII by the reaction with an appropriate boron electrophile such as e.g. boronic acid ester, haloboronic acid ester, alkylbornic acid ester, dialkylboronic acid ester, trihaloborane, and derivatives thereof. In addition, the boronylated aromatic compound XVII may also be prepared from the corresponding chlorinated, brominated, iodinated, or pseudohalogenated such as e.g. trifluoromethanesulfonated and tosylated precursor and a diboron compound such e.g. bis(pinacolato)diboron and bis(neopentyl-glycolato)diboron, or a borane such as e.g. pinacolborane through a transition metal catalyzed reaction (see e.g. *Tetrahedron Lett.* 2003, p. 4895-4898 and references quoted therein). The transition metal is e.g. palladium that is employed as element, salt, or complex; common Pd sources are e.g. palladium on charcoal, palladium acetate, palladium chloride, palladium bromide, palladium dibenzylideneacetone that are used as such or in combination with a ligand such as e.g. phosphines such as e.g. tricyclohexylphosphine, triphenylphosphine, 1,1'-bis(diphenyl-phosphino)ferrocene, and tritolylphosphine, or phosphites or imidazolium salts such as 1,3-diaryl or dialkylimidazolium halides or pseudohalides or dihydroimidazolium salts. The resulting complex of the transition metal and the ligand may be prepared in situ or in a separate step. The reactions are preferably conducted in the presence of a base such as e.g. triethylamine, potassium acetate, potassium carbonate, potassium phosphate, sodium hydroxide, triethylamine or ethyldiisopropylamine, in solvents such as e.g. acetonitrile, tetrahydrofuran, dimethylsulfoxide, dimethylformamide, dimethylacetamide, N-methyl-pyrrolidone, dioxane, toluene and mixtures thereof at 0 to 180° C., preferably at 60 to 140° C. The lithium or magnesium substituted phenyl compounds XVII add spontaneously to benzaldehyde XVIII furnishing diarylmethanol XIX. This reaction can be performed in solvents such as diethylether, tetrahydrofuran, toluene, dichloromethane, dioxane, hydrocarbons such as e.g. hexane and mixtures thereof at temperatures ranging from −100 to 20° C., preferably at −80 at 0° C. Aryl boronic acids XVII can be added to the benzaldehyde derivative XVIII by means of a rhodium catalyzed reaction furnishing the respective diarylmethanol XIX (see e.g. *Adv. Synth. Catal.* 2001, p. 343-350 and references quoted therein). The concluding step in Scheme 7 is the reduction of the diarylmethanol XIX to the aglycon V. Suitable reducing agents for this transformation are e.g. $NaBH_4$, $LiAlH_4$, $iBu_2AlH$, $Et_3SiH$, $iPr_3SiH$ or $Ph_2SiClH$. The reaction is usually carried out in the presence of a Lewis acid such as for example $BF_3{*}OEt_2$, trifluoroacetic acid, hydrochloric acid, $InCl_3$, or $AlCl_3$ in a solvent such as halogenated hydrocarbons such as e.g. dichloromethane or 1,2-dichloro-ethane, toluene, hydrocarbons such as e.g. hexane, acetonitrile or mixtures thereof at temperatures of −80 to 150° C., preferably at −20 to 100° C. Reductions with hydrogen in the presence of a transition metal catalyst such as e.g. Pd on charcoal are principally also possible though particular care has to be taken using this method to preserve full integrity of the rest of the molecule.

Scheme 7: Synthesis of Aglycon V - Approach 5

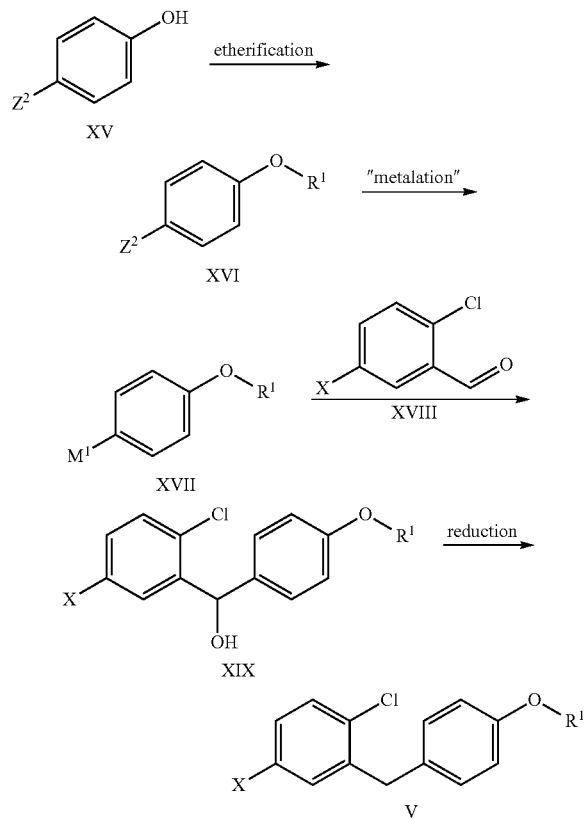

$M^1$ = Li, MgHal, ZnHal, InHal$_2$, CrHal$_2$,
B(OH)$_2$, BR$_2$, CeHal$_2$
$Z^2$ = Hal, OSO$_2$R, OSO$_2$CF$_3$
Hal = Cl, Br, I $M^1$ = Li, MgHal, ZnHal, InHal$_2$, CrHal$_2$,
B(OH)$_2$, BR$_2$, CeHal$_2$
$Z^2$ = Hal, OSO$_2$R, OSO$_2$CF$_3$
Hal = Cl, Br, I

The synthesis sketched in Scheme 8 begins with the addition of metalated phenylether derivative XXI to benzoic acid or a derivative thereof (XX) such as benzoic acid esters, benzoic acid anhydrides, benzamides such as e.g. of the Weinreb type, benzonitriles, or benzoyl chlorides to deliver the benzophenone VII. Lithium or magnesium derivatized phenylethers XXI can principally be added to benzamides, benzoic acid esters, benzoyl chlorides, benzoic acid anhydrides, and benzonitriles to give the desired benzophenone VII while only lithiated phenylethers react with benzoic acids to produce the same compound. The latter reaction can be carried out in e.g. tetrahydrofuran, dioxane, diethylether, benzene, toluene, hexane and mixtures thereof at −80 to 100° C., preferably at −30 to 40° C. Benzonitriles and benzamides such as e.g. the corresponding Weinreb-type amide or a close derivative thereof are preferentially reacted in tetrahydrofuran, dioxane, toluene, hexane, ether and mixtures thereof at temperatures ranging from −90 to 50° C., preferably at −80 to 20° C. Benzoyl chlorides or anhydrides and benzoic acid esters are commonly employed in inert solvents such as tetrahydrofuran, diethylether, toluene, dichloromethane, dioxane, hydrocarbons such as e.g. hexane or mixtures of them at low temperatures, preferably at −80 to 0° C. To prevent double addition of the organometal compound to benzoyl chlorides, benzoyl anhydrides or benzoic acid esters to produce the corresponding alcohol the addition may superiorly carried out in the presence of a trapping reagent such as e.g. trimethylsilyl chloride. An alternative choice to prevent double addition in the cases mentioned may be transmetalation to a less reactive nucleophile XXI. Suitable metals are e.g. zinc, cerium, chromium, or indium that are introduced as e.g. chloride, bromide, iodide or pseudo halide salt such as e.g. trifluoromethanesulfonate to transmetalate the lithium or magnesium compound to give the corresponding less reactive, more selective metal compound XXI. The transmetalation is preferentially conducted in the solvent wherein the initial organometal compound is generated (see above) at temperatures of −90 to 0° C. Transmetalation is not restricted to the metals mentioned and the boron derivatized compounds already described in Scheme 7 but can also furnish e.g. stannanes and silanes. Some of the transmetalated compounds react spontaneously with the corresponding benzoyl electrophile, particularly benzoyl chloride and anhydride, but the addition of a transition metal catalyst may be advantageous. In particular arylboronic acids, esters thereof, dialkylarylboranes, aryltrifluoroborates, stannanes, silanes, indium, chromium, and zinc derivatized compounds XXI couple with benzoyl chloride derivatives XX mediated by a transition metal such as e.g. palladium, copper, iron, nickel, that may be used as element or salt such as e.g. acetate, chloride, bromide, iodides, acetylacetonate, trifluoromethanesulfonate, and cyanide in combination with ligands such as e.g. phosphites, phosphines such as e.g. triphenylphosphine, tricyclohexylphoshine, tritolylphosphine, 1,3-substituted imidazolium or dihydroimidazolium compounds delivering diarylketones VII. The active transition metal species can be prepared prior to the addition to the coupling partners but also in the presence of the reaction partners in situ. Suitable solvents are e.g. dimethylformamide, dimethylacetamide, N-methylpyrrolidone, dimethylsulfoxide, dioxane, ether, hexane, toluene, tetrahydrofuran, dichloromethane or mixtures thereof that are preferably used at −50 to 150° C., particularly preferably at 0 to 120° C. The concluding conversion to get to the aglycon V has been detailed above and can be applied analogously here.

Scheme 8: Synthesis of Aglycon V - Approach 6

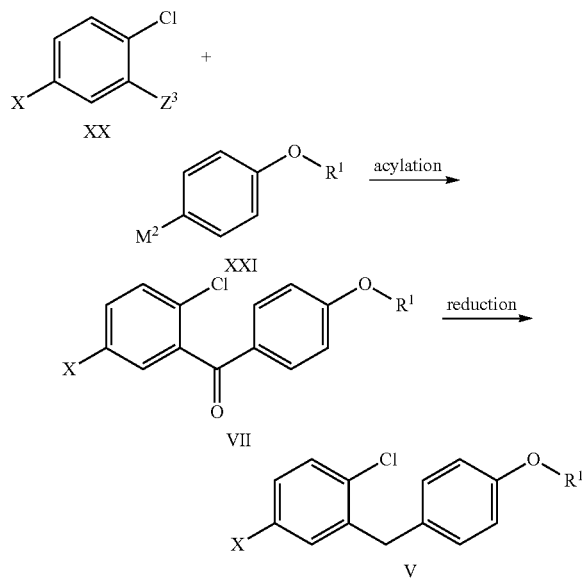

Z³ = e.g. COOH, COOR, CONR₂,
   CONROR, CN, COCl
M² = e.g. Li, MgHal, B(OH)₂, BR₂, SiR₃,
   SnR₃, CeHal₂, InHal₂, ZnHal
Hal = I, Br, Cl

Z³ = e.g. COOH, COOR, CONR₂,
   CONROR, CN, COCl
M² = e.g. Li, MgHal, B(OH)₂, BR₂, SiR₃,
   SnR₃, CeHal₂, InHal₂, ZnHal
Hal = I, Br, Cl

According to the Scheme 9 the metalated aryl groups XXIII that can be synthesized as described above can also be reacted with benzyl electrophiles XXII such as e.g. benzyl chlorides, bromides, iodides, sulfonates, phosphonates, carbonates, or carboxylates affording diarylmethanes V. Lithium or magnesium derivatized phenyl compounds XXIII are reacted favorably (but not always necessarily) in the presence of a transition metal such as e.g. copper, iron, nickel, or palladium (see e.g. *Org. Lett.* 2001, 3, 2871-2874 and *Tetrahedron Lett.* 2004, p. 8225-8228 and references cited therein). Usable solvents are e.g. tetrahydrofuran, dioxane, toluene, dichloromethane, hexane, ether or mixtures thereof. The range of reaction temperature is from −90 to 20° C., preferably from −80 to −20° C. The transition metal can be employed as element such as e.g. on charcoal, as salt such as e.g. acetate, acetylacetonate, cyanide, chloride, bromide, iodide, trifluoromethanesulfonate, or as complex such as e.g. with dibenzylideneacetones, phosphites, phosphines such as e.g. triphenylphosphine, tricyclohexylphoshine, and tritolylphosphine, or with carbenes derived from e.g. 1,3-disubstituted imidazolium or dihydroimidazolium compounds. The active transition metal species can be prepared in situ in the presence of the reaction partners or prior to the addition to the coupling partners. Arylmetal compounds XXIII bearing e.g. boron, tin, silicon, zinc, indium, chromium residue are preferably used in combination with a transition metal catalyst. Suitable metal compounds of these types are e.g. boronic acids, boronic acid esters, dialkylboranes, trifluoroborates, trialkylstannanes, trichlorostannanes, trialkoxysilanes, dihaloindium substituted or halozinc substituted compounds. The metal substituted compounds XXIII may be synthesized as described before by transmetalation from the corresponding lithium or magnesium derivatized compounds or as in the case of zinc, chromium and indium also directly from the corresponding arylchloride, bromide or iodide by insertion of the elemental metal. The coupling reaction with the benzyl electrophile may be conducted in tetrahydrofuran, dimethylformamid, dimethylacetamid, N-methyl-pyrrolidone, dimethylsulfoxide, toluene, ether, dioxane, dichloromethane, acetonitrile, hexane, water, alcohols such as e.g. ethanol, isopropanol, or mixtures thereof at reaction temperatures of −30 to 180° C., preferably at 20 to 150° C. Depending on the metal an additional base such as e.g. triethylamine, ethyldiisopropylamine, cesium or potassium or sodium or lithium carbonate, potassium or sodium or lithium teributoxide, potassium phosphate, potassium or cesium or tetrabutylammonium fluoride, sodium hydroxide, thallium hydroxide, sodium methoxide and/or other additives such as e.g. lithium chloride, silver salts such as e.g. carbonate or oxide, tetrabutylammonium bromide, and sodium bromide may be advantageous or even essential (e.g. M. Schlosser, Organometallics in Synthesis, John Wiley & Sons, Chichester/New York/Brisbane/Toronto, 1994 and references cited therein).

Scheme 9: Synthesis of Aglycon V - Approach 7

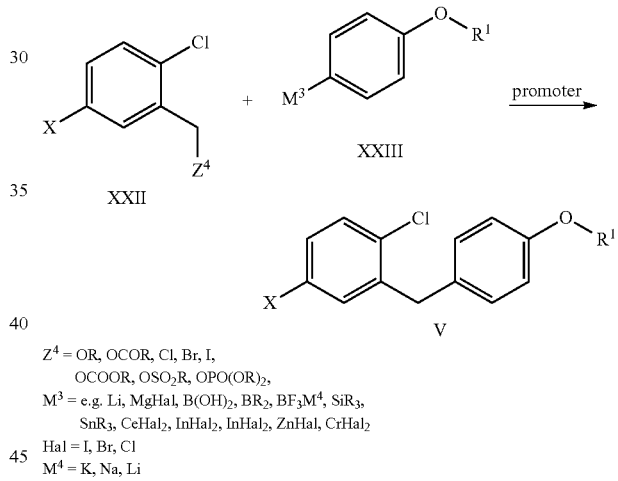

Z⁴ = OR, OCOR, Cl, Br, I,
   OCOOR, OSO₂R, OPO(OR)₂,
M³ = e.g. Li, MgHal, B(OH)₂, BR₂, BF₃M⁴, SiR₃,
   SnR₃, CeHal₂, InHal₂, InHal₂, ZnHal, CrHal₂
Hal = I, Br, Cl
M⁴ = K, Na, Li

The Scheme 10 shows the access to aglycon V via intermediate XXVI that can be prepared according to Scheme 8. If Z⁵ represents halogen such as F, intermediate XXVI may alternatively be prepared by Friedel-Crafts-acylation according to scheme 5. Replacement of Z⁵ in compound XXVI by O—R¹ may be achieved via different methods. In the cases in which Z⁵ preferably denotes fluorine, chlorine, iodine, trifluormethylsulfonate O—R¹ may be attached according to a nucleophilic substitution on an aromatic ring in which R¹—OH or an anion thereof replaces Z⁵ in an addition/elimination sequence. The reaction is usually conducted in solvents such as e.g. dimethylformamide, dimethylacetamide, dimethylsulfoxide, tetrahydrofuran, dioxane, teributanol, toluene, N-methylpyrrolidone, water, alcohol or mixtures thereof in the presence of a base such as e.g. lithium or sodium or potassium teributoxide, sodium or potassium or cesium carbonate, sodium or potassium hydroxide, tripotassium phosphate, triethylamine, ethyldiisopropylamine, or diazabicycloundecene at temperatures ranging from 0 to 180° C., preferably at 40 to 140° C. R¹—OH may also be used as solvent and may be deprotonated with e.g. sodium hydride or sodium to form the alkoxide prior the addition of compound XXVI. To enhance the nucleophilicity of $R^1$—O-metal the addition of crown ethers such as e.g. 18-crown-6 may be useful. The coupling of isolatable intermediate XXVI and $R^1$—OH may also be conducted in the presence of a transition metal salt or complex such as e.g. derived from Pd or Cu (Ullmann or Ullmann-type reaction). Here $Z^5$ preferentially stands for iodine or trifluoromethansulfonate. The same solvents, bases, additives, and temperatures described for the uncatalyzed reaction may be used for the catalyzed reaction except for that the latter is preferably executed under an inert gas atmosphere such as argon or nitrogen. The catalyst is usually employed as element as such or on charcoal, as a salt such as e.g. chloride, bromide, acetate, cyanide, or as a complex with ligands such as e.g. phosphites, phosphines, dibenzylideneacetone, 1,3-disubstituted imidazole or dihydroimidazole carbenes. If $Z^5$ denotes arylboronic acid or trifluoroborate $R^1$—OH may be attached via a copper(II) catalyzed reaction with a copper source such as e.g. copper (II) acetate in the presence of a base such as e.g. triethylamine or pyridine in solvents such as e.g. tetrahydrofuran, dichloromethane, 1,2-dichloroethane, acteonitrile, dioxane, dimethylformamide, dimethylacetamide, and N-methylpyrrolidone. The reaction may be carried out with stoichiometric amounts of copper catalyst or in the presence of a co-oxidant such as e.g. oxygen, pyridine-N-oxide, or tetramethylpiperidineoxide with only catalytic amounts of the catalyst. Dry solvents and the presence of drying agents such as e.g. molecular sieves are advantageous (see e.g. *Angew. Chem.* 2003, 115, pp. 5558-5607 and references quoted therein).

Scheme 10: Synthesis of Aglycon V - Approach 8

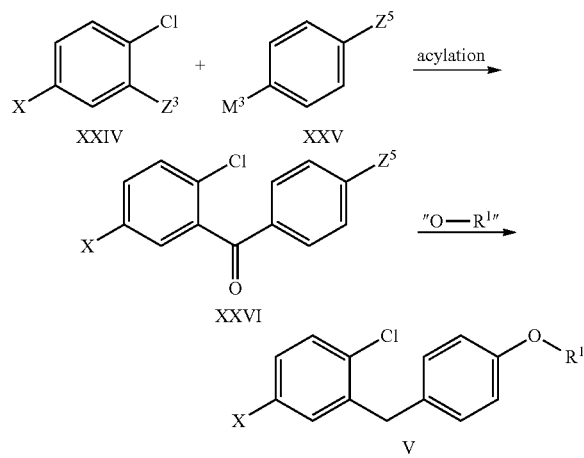

$Z^3$ = e.g. COOH, COOR, $CONR_2$, CONROR, CN, COCl
$M^3$ = e.g. Li MgHal, $B(OH)_2$, $BR_2$, $BF_3M^4$, $SiR_3$, $SnR_3$, $CeHal_2$, $InHal_2$, $InHal_2$, $ZnHal$, $CrHal_2$
Hal = I, Br, Cl
$M^4$ = Li, Na, K
$Z^5$ = e.g. F, Cl, I, $B(OH)_2$, $BF_3K$, $BF_3Na$, $OSO_2CF_3$

The Scheme 11 shows a preferred access to the aglycon V which corresponds to the Scheme 10 whereby the intermediate XXVI is prepared by Friedel-Crafts-acylation according to Scheme 5. The Scheme 11 and the following sections describe preferred conditions and embodiments of the seventh aspect of this invention.

The assembly of aglycon V starts from the known benzoyl chloride XII and halobenzene XXVII. The substituent X preferably denotes a bromine or iodine atom. A preferred meaning of the substituent $Z^5$ is a fluorine atom. The first step, the preparation of benzophenone XXVI, can be characterized as Friedel-Crafts or Friedel-Crafts-type acylation, a well-known method in organic synthesis. In principal, the benzoyl chloride XII may be replaced by other benzoic acid derivatives such as e.g. benzoyl anhydrides, esters, or benzonitriles. This reaction is advantageously carried out in the presence of a catalyst such as e.g. $AlCl_3$, $FeCl_3$, iodine, iron, $ZnCl_2$, sulfuric acid, or trifluoromethanesulfonic acid, all of which are used in catalytic or up to stoichiometric amounts. A preferred catalyst is $AlCl_3$. The reaction may be performed with or without additional solvents. Preferred additional solvents are chlorinated hydrocarbons such as e.g. dichloromethane or 1,2-dichloroethane, hydrocarbons such as e.g. hexane or mixtures thereof. According to a preferred embodiment the reaction is carried out using an excess of the halobenzene XXVII which additionally serves as a solvent. Preferred temperatures during the reaction range from −30 to 140° C., preferably from 30 to 85° C. After completion of the reaction the reaction mixture may be quenched with water. Preferably the organic solvents are removed. The intermediate XXVI may be isolated, preferably by crystallization, for example from water.

The second reaction step in Scheme 11 which is the replacement of $Z^5$ by O—$R^1$ is analogous to the second reaction step in Scheme 10 as described hereinbefore. According to a preferred embodiment O—$R^1$ is attached according to a nucleophilic substitution on an aromatic ring in which $R^1$—OH or an anion thereof replaces $Z^5$ in an addition/elimination sequence. The reaction is advantageously conducted in a solvent such as e.g. dimethylformamide, dimethylacetamide, dimethylsulfoxide, tetrahydrofuran, dioxane, teributanol, toluene, heptane, N-methylpyrrolidone, water, alcohol or a mixture thereof. Preferred solvents are selected from dimethylformamide, tetrahydrofuran and dimethylacetamide.

This reaction is preferably carried out in the presence of a base such as alkali $C_{1-4}$-alkoxides, alkali carbonates, alkali hydroxides, alkali phosphates, tri($C_{1-3}$ alkyl)amines and other N-containing organic bases. Examples of preferred bases are lithium or sodium or potassium teributoxide, sodium or potassium or cesium carbonate, sodium or potassium hydroxide, tripotassium phosphate, triethylamine, ethyldiisopropylamine, sodium bis(trimethylsilyl)amide (NaHMDS), diazabicycloundecene (DBU), 1,4-diazabicyclo[2.2.2]octane (DABCO) or mixtures thereof. More preferred bases are selected from sodium or potassium teributoxide, sodium or potassium hydroxide, cesium carbonate, a mixture of cesium carbonate and potassium carbonate, or mixtures thereof. The amount of the base is preferably in the range from 1 to 5 mol base per mol of intermediate XXVI. In case the base is a carbonate, phosphate or mixtures thereof, the total amount of the base is more preferably in the range from 2 to 4 mol base, most preferably about 3 mol base per mol of intermediate XXVI.

The reaction is preferably carried out at temperatures ranging from about −20 to 60° C., more preferably from about −10 to 40° C., even more preferably from about 0 to 30° C.

The intermediate VII may be isolated from the reaction mixture, preferably by crystallization, for example from a mixture of ethanol and water.

The synthetic route according to Scheme 11 concludes with the reduction of benzophenone VII to furnish aglycon V. Suitable reducing agents for this conversion are silanes, in particular tri($C_{1-3}$-alkyl)silanes, such as e.g. triethylsilane, dimethylethylsilane and triisopropylsilane, borohydrides such as e.g. $NaBH_4$, and aluminum hydrides such as e.g. $LiAlH_4$ in the presence of a Lewis acid such as for example $BF_3$*$OEt_2$, tris(pentafluorophenyl)borane, trifluoroacetic acid, hydrochloric acid, aluminum chloride, or $InCl_3$. A particularly preferred reducing agent is $Et_3SiH$ in the presence of a Lewis acid such as for example $BF_3$*$OEt_2$. Another particularly preferred reducing agent is $NaBH_4$ in the presence of a Lewis acid such as for example trifluoroacetic acid.

The amount of the reducing agent, in particular of $Et_3SiH$, is preferably from about 1 to 5 mol, even more preferably from about 2 to 4 mol, most preferably about 3 mol per mol of benzophenone VII. The amount of the Lewis acid, in particular of $BF_3$*$OEt_2$, is preferably from about 1 to 5 mol, even more preferably from about 1 to 3 mol per mol of benzophenone VII.

The reduction reaction is preferably carried out in a solvent such as halogenated hydrocarbons, for example dichloromethane and 1,2-dichloroethane, toluene, benzene, hexane, acetonitrile and mixtures thereof.

Preferably the reduction is performed at temperatures from about −30 to 100° C., preferably from about −20 to 50° C., even more preferably from about −10 to 25° C.

The aglycon of the formula V may be isolated and purified or may be used in the synthesis of the final product of the formula I without further purification.

Starting from the aglycon of the formula V the product of the formula I may be obtained using the methods as described hereinbefore, preferably using the methods depicted and described in Scheme 2a.

Scheme 11: Synthesis of Aglycon V - Preferred embodiment

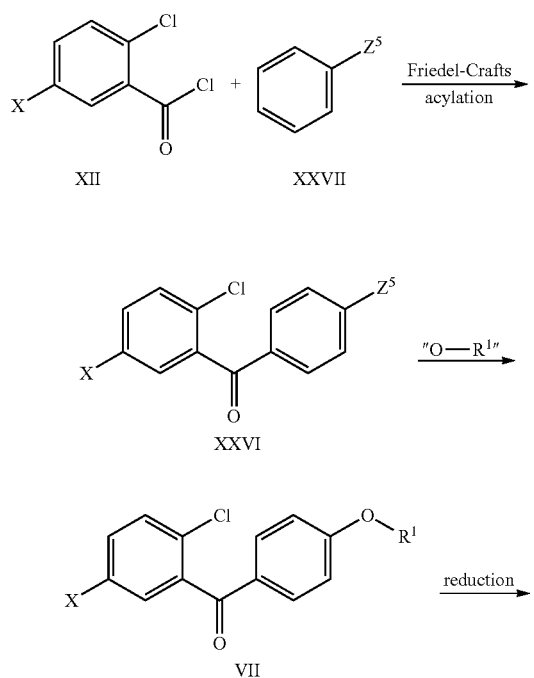

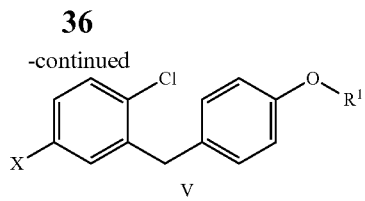

$Z^5$ = F, Cl, I

In the reactions described hereinbefore, any reactive group present such as ethynyl, hydroxy, amino, alkylamino or imino groups may be protected during the reaction by conventional protecting groups which are cleaved again after the reaction.

For example, a protecting group for a hydroxy group may be a trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Moreover, the compounds and intermediates obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds and intermediates obtained which occur as racemates may be separated by methods known per se (cf. Allinger N. L. and Eliel E. L. in "Topics in Stereochemistry", Vol. 6, Wiley Interscience, 1971) into their optical antipodes and compounds or intermediates with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+) or (−)-menthyloxycarbonyl.

Furthermore, the compounds and intermediates of the present invention may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds according to the invention are advantageously also obtainable using the methods described in the examples that follow, which may also be combined for this purpose with methods known to the skilled man from the literature, for example, particularly the methods described in WO 98/31697, WO 01/27128, WO 02/083066, WO 03/099836 and WO 2004/063209.

In the foregoing and following text, H atoms of hydroxyl groups are not explicitly shown in every case in structural formulae. The Examples that follow are intended to illustrate the present invention without restricting it. In case the pressure is indicated in the unit "Torr", the corresponding values can be converted into SI units by using 1 torr=133.322 Pa. The terms "room temperature" or "ambient temperature" denote a temperature of about 20° C.

| | |
|---|---|
| Ac | acetyl, |
| Bu | butyl, |
| Et | ethyl, |
| EtOAc | ethylacetate, |
| i-Pr | iso-propyl, |
| Me | methyl, |
| MeOH | methanol, |
| MTBE | methyl-tertbutylether, |
| THF | tetrahydrofuran. |

EXPERIMENTAL PROCEDURES

Example I

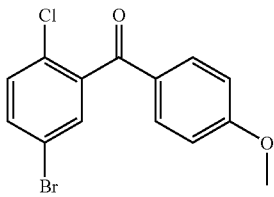 [SMILES: COc1ccc(C(=O)c2cc(Br)ccc2Cl)cc1]

(5-bromo-2-chloro-phenyl)-(4-methoxy-phenyl)-methanone 38.3 ml oxalyl chloride and 0.8 ml of dimethylformamide are added to a mixture of 100 g of 5-bromo-2-chloro-benzoic acid in 500 mL dichloromethane. The reaction mixture is stirred for 14 h, then filtered and separated from all volatile constituents in a rotary evaporator. The residue is dissolved in 150 ml dichloromethane, the resulting solution is cooled to −5° C., and 46.5 g of anisole are added. Then 51.5 g of aluminum trichloride are added batchwise so that the temperature does not exceed 5° C. The solution is stirred for another 1 h at 1 to 5° C. and then poured onto crushed ice. The organic phase is separated, and the aqueous phase is extracted three times with dichloromethane. The combined organic phases are washed with aqueous 1 M hydrochloric acid, twice with 1 M sodium hydroxide solution, and with brine. The organic phase is dried, the solvent is removed in vacuo, and the residue is recrystallized from ethanol.

Yield: 86.3 g (64% of theory)

Mass spectrum (ESI$^+$): m/z=325/327/329 (Br+Cl) [M+H]$^+$

The following compounds may be obtained analogously to Example I:

(1) (5-bromo-2-chloro-phenyl)-(4-(R)-tetrahydrofuran-3-yloxy-phenyl)-methanone

The reaction is carried out according to the procedure described above except for 2 equivalents of aluminum trichloride are used. The reaction mixture is stirred at room temperature after the addition of aluminum trichloride.

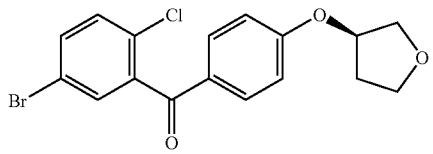 [SMILES: O=C(c1ccc(O[C@@H]2CCOC2)cc1)c1cc(Br)ccc1Cl]

Mass spectrum (ESI$^+$): m/z=382/384/386 (Br+Cl) [M+H]$^+$ (2) (5-bromo-2-chloro-phenyl)-(4-(S)-tetrahydrofuran-3-yloxy-phenyl)-methanone The reaction is carried out according to the procedure described above except for 2 equivalents of aluminum trichloride are used. The reaction mixture is stirred at room temperature after the addition of aluminum trichloride.

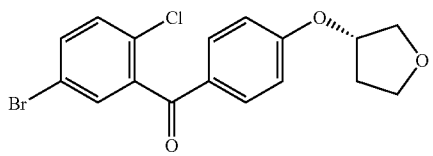 [SMILES: O=C(c1ccc(O[C@H]2CCOC2)cc1)c1cc(Br)ccc1Cl]

Example II

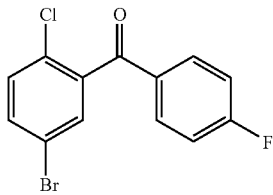 [SMILES: O=C(c1ccc(F)cc1)c1cc(Br)ccc1Cl]

(5-bromo-2-chloro-phenyl)-(4-fluoro-phenyl)-methanone

Variant A:

8.7 mL oxalyl chloride and 0.3 mL of dimethylformamide are added to a mixture of 24 g of 5-bromo-2-chloro-benzoic acid in 150 mL dichloromethane. The reaction mixture is stirred for 14 h, then filtered and separated from all volatile constituents in a rotary evaporator. The residue is dissolved in 105 mL fluorobenzene and heated to 85° C. Then 13.3 g of aluminum trichloride are added batchwise and the resultant mixture is stirred for 16 h at 85° C. After cooling to ambient temperature, the reaction mixture is poured onto a mixture of 300 g crushed ice and 100 mL concentrated hydrochloric acid. The resultant mixture is extracted two times with ethyl acetate. The combined organic extracts are washed with aqueous 1 M sodium hydroxide solution, aqueous 1 M hydrochloric acid and brine. After drying over magnesium sulfate the solvent is removed in vacuo. The solidified residue is washed with petrol ether and dried in vacuo.

Yield: 25.0 g (80% of theory)

Mass spectrum (ESI⁺): m/z=313/315/317 (Br+Cl) [M+H]⁺

Variant B:

To a solution of 9.42 g 5-bromo-2-chloro-benzoic acid in 40 mL of fluorobenzene and 0.1 mL of N,N-dimethylformamide is added 4 mL of oxalyl chloride at 0 to 10° C. The solution is stirred at about 20° C. for 2 hours. The excess amount of oxalyl chloride is evaporated. The residue is diluted in 38 mL of fluorobenzene and 5.87 g of aluminum chloride is added at 0° C. in five portions. The solution is stirred at 80° C. for 5 hours and quenched with 60 mL of water at 0 to 25° C. The product is extracted in 50 mL of isopropylacetate and washed with two times of 40 mL 3 weight-% brine. The solvent is removed upon evaporation and the product is crystallized from heptane and water.

Yield: 11.94 g (92.4% of theory)

Mass spectrum (ESI⁺): m/z=314/316 (Cl) [M+H]⁺

Example III

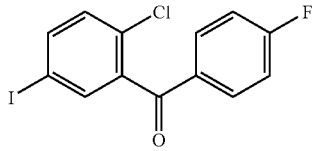 [SMILES: O=C(c1ccc(F)cc1)c1cc(I)ccc1Cl]

(2-Chloro-5-iodo-phenyl)-(4-fluoro-phenyl)-methanone

To a solution of 48.94 g 2-chloro-5-iodo-benzoic acid in 180 mL of fluorobenzene and 0.3 mL of N,N-dimethylformamide is added 16.2 mL of oxalyl chloride at 0 to 10° C. The solution is stirred at about 20° C. for 2 hours. The excess amount of oxalyl chloride is evaporated. The residue is diluted in 166 mL of fluorobenzene and 25.93 g of aluminum chloride is added at 0° C. in five portions. The solution is stirred at 75° C. for 1.5 hours and quenched with 300 mL of water at 0 to 25° C. The product is extracted in 300 mL of isopropylacetate and washed with two times of 200 mL brine (3 weight-%). The residue water and solvent is removed upon evaporation.

Yield: 60.56 g (95% of theory)

Mass spectrum (ESI⁺): m/z=361/363 (Cl)[M+H]⁺

Example IV

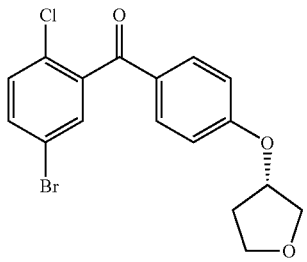 [SMILES: O=C(c1ccc(O[C@H]2CCOC2)cc1)c1cc(Br)ccc1Cl]

(5-bromo-2-chloro-phenyl)-(4-(S)-tetrahydrofuran-3-yloxy-phenyl)-methanone

Variant A:

To a solution of 8.1 g (S)-3-hydroxy-tetrahydrofuran in 200 ml dimethylformamide are added 10.3 g potassium tert-butoxide. The mixture is stirred at room temperature for 10 min and then 24.0 g (5-bromo-2-chloro-phenyl)-(4-fluoro-phenyl)-methanone are added so with cooling in a water bath that the solution temperature remained below 35° C. The reaction mixture is stirred for 14 h at room temperature and then diluted with 1000 mL water. The resultant mixture is extracted with ethyl acetate and the combined extracts are washed with water and brine. After drying over magnesium sulfate the solvent is removed and the residue is recrystallized from ethanol.

Yield: 22.5 g (77% of theory)

Mass spectrum (ESI⁺): m/z=382/384/386 (Br+Cl) [M+H]⁺

Variant B:

To a solution of 19.00 g (5-bromo-2-chloro-phenyl)-(4-fluoro-phenyl)-methanone in 60 mL of tetrahydrofuran and 5.87 g of (S)-3-hydroxytetrahydrofuran is added 9.60 g of potassium tert-butoxide in 90 mL of tetrahydrofuran at 0 to 5° C. The solution is stirred at 10° C. for 0.5 hour. The reaction is quenched with 60 mL of water and 40 mL of methyl tert-butyl ether at 0 to 25° C. The product is washed with 80 mL of brine (3 weight-%). The solvent is removed upon evaporation and crystallized in 135 mL of 2:1 isopropylacetate/water.

Yield: 20.1 g (87% of theory)

Mass spectrum (ESI⁺): m/z=382/384 (Cl) [M+H]⁺

Example V

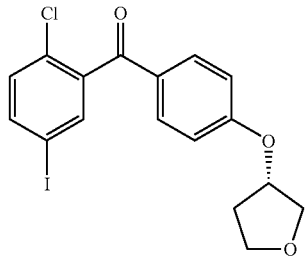 [SMILES: O=C(c1ccc(O[C@H]2CCOC2)cc1)c1cc(I)ccc1Cl]

(2-Chloro-5-iodo-phenyl)-{4-[(S)-(tetrahydrofuran-3-yl)oxy]-phenyl}-methanone

To a solution of 60.56 g (2-chloro-5-iodo-phenyl)-(4-fluoro-phenyl)-methanone in 170 mL of tetrahydrofuran and 16.46 g of (S)-3-hydroxytetrahydrofuran is added 26 g of potassium tert-butoxide in 250 mL of tetrahydrofuran at 0 to 5° C. The solution is stirred at 10° C. for 0.5 hour. The reaction is quenched with 170 mL of water and 170 mL of methyl tert-butyl ether at 0 to 25° C. The product is washed with 170 mL of brine (3 weight-%). The solvent is removed upon evaporation and crystallized in 220 mL of iso-propylacetate.

Yield: 65.1 g (90% of theory)

Mass spectrum (ESI⁺): m/z=428/430 (Cl) [M+H]⁺

Example VI

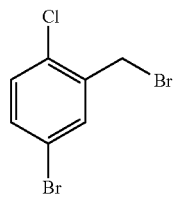

4-bromo-2-bromomethyl-1-chloro-benzene 4.0 g N-bromosuccinimide are slowly added to a solution of 5.0 g of 4-bromo-1-chloro-2-hydroxymethyl-benzene and 5.9 g triphenylphosphine in 50 mL of tetrahydrofuran chilled to 5° C. After 1 h stirring at ambient temperature the precipitate is filtered off, and the solvent is eliminated in vacuo. The residue is purified by chromatography on silica gel (cyclohexane/ethyl acetate 50:1).

Yield: 4.9 g (76% of theory)
Mass spectrum (EI): m/z=282/284/286 (Br+Cl) [M]$^+$

Example VII

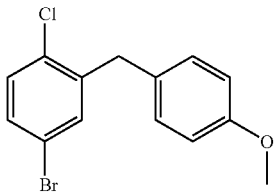

4-bromo-1-chloro-2-(4-methoxy-benzyl)-benzene

A solution of 86.2 g (5-bromo-2-chloro-phenyl)-(4-methoxy-phenyl)-methanone and 101.5 mL triethylsilane in 75 mL dichloromethane and 150 mL acetonitrile is cooled to 10° C. 50.8 mL of boron trifluoride etherate are added so that the temperature does not exceed 20° C. The solution is stirred for 14 h at ambient temperature, before another 9 mL triethylsilane and 4.4 mL boron trifluoride etherate are added. The solution is stirred for a further 3 h at 45 to 50° C. and then cooled to ambient temperature. A solution of 28 g potassium hydroxide in 70 mL of water is added, and the resultant mixture is stirred for 2 h. Then the organic phase is separated, and the aqueous phase is extracted three times with diisopropylether. The combined organic phases are washed twice with 2 M potassium hydroxide solution and once with brine and then dried over sodium sulfate. After the solvent is removed, the residue is washed with ethanol and dried at 60° C.

Yield: 50.0 g (61% of theory)
Mass spectrum (ESI$^+$): m/z=310/312/314 (Br+Cl) [M+H]$^+$ The following compounds may be obtained analogously to Example VII:

(1) 4-bromo-1-chloro-2-(4-cyclopentyloxy-benzyl)-benzene

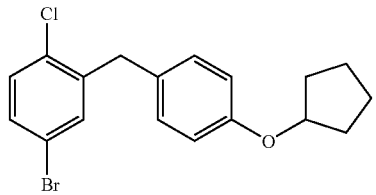

(2) (S)-4-bromo-1-chloro-2-(4-tetrahydrofuran-3-yloxy-benzyl)-benzene

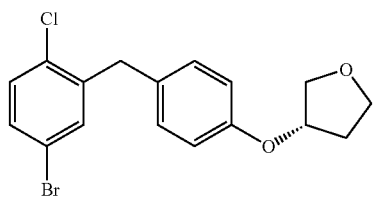

(3) (R)-4-bromo-1-chloro-2-(4-tetrahydrofuran-3-yloxy-benzyl)-benzene

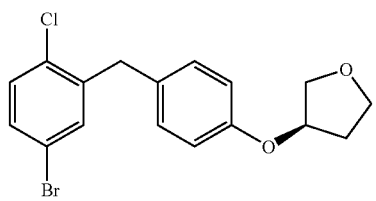 [SMILES: Clc1ccc(Br)cc1Cc1ccc(O[C@@H]2CCOC2)cc1]

(4) 4-bromo-1-chloro-2-(4-tetrahydropyran-4-yloxy-benzyl)-benzene

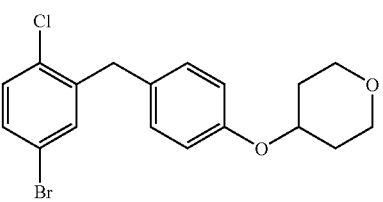 [SMILES: Clc1ccc(Br)cc1Cc1ccc(OC2CCOCC2)cc1]

(5) 4-bromo-1-chloro-2-(4-cyclohexyloxy-benzyl)-benzene

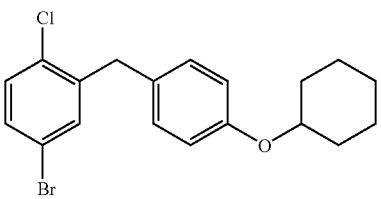 [SMILES: Clc1ccc(Br)cc1Cc1ccc(OC2CCCCC2)cc1]

(6) 4-bromo-1-chloro-2-(4-cyclobutyloxy-benzyl)-benzene

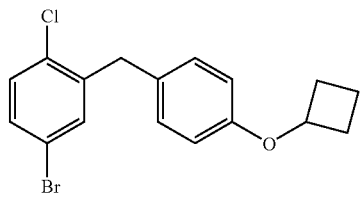 [SMILES: Clc1ccc(Br)cc1Cc1ccc(OC2CCC2)cc1]

Example VIII

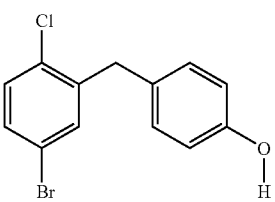 [SMILES: Oc1ccc(Cc2cc(Br)ccc2Cl)cc1]

4-(5-bromo-2-chloro-benzyl)-phenol

A solution of 14.8 g 4-bromo-1-chloro-2-(4-methoxy-benzyl)-benzene in 150 ml dichloromethane is cooled in the ice bath. Then 50 ml of a 1 M solution of boron tribromide in dichloromethane are added, and the solution is stirred for 2 h at ambient temperature. The solution is then cooled in the ice bath again, and saturated potassium carbonate solution is added dropwise. At ambient temperature the mixture is adjusted with aqueous 1 M hydrochloric acid to a pH of about 1, the organic phase is separated off and the aqueous phase is extracted another three times with ethyl acetate. The combined organic phases are dried over sodium sulphate, and the solvent is removed completely.

Yield: 13.9 g (98% of theory)
Mass spectrum (ESI$^{31}$): m/z=295/297/299 (Br+Cl) [M−H]$^-$ Example IX

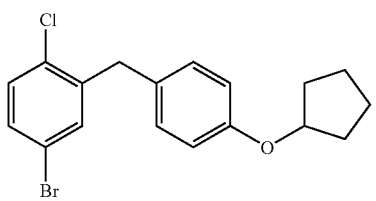

4-Bromo-1-chloro-2-(4-cyclopentyloxy-benzyl)-benzene

To a mixture of 40.0 g 4-(5-bromo-2-chloro-benzyl)-phenol and 71.0 g cesium carbonate in 300 mL ethanol are added 23 mL iodocyclopentane. The mixture is stirred at 60° C. over night and then cooled to ambient temperature. The ethanol is evaporated, and water is added to the residue. The resulting mixture is extracted with ethyl acetate, the combined extracts are dried over sodium sulfate, and the solvent is removed. The residue is filtered through silica gel (cyclohexane/ethyl acetate 100:1→10:1).

Yield: 34.4 g (70% of theory)
Mass spectrum (ESI$^+$): m/z=364/366/368 (Br+Cl) [M]$^+$ The following compounds may be obtained analogously to Example IX:

(1) (S)-4-bromo-1-chloro-2-(4-tetrahydrofuran-3-yloxy-benzyl)-benzene

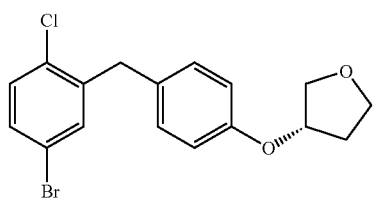 [SMILES: Clc1ccc(Br)cc1Cc1ccc(O[C@H]2CCOC2)cc1]

Mass spectrum (ESI$^+$): m/z=366/368/370 (Br+Cl) [M+H]$^+$ (2) (R)-4-bromo-1-chloro-2-(4-tetrahydrofuran-3-yloxy-benzyl)-benzene

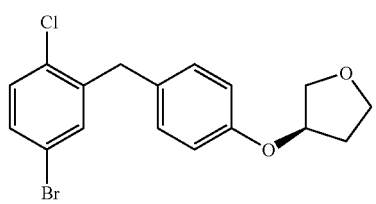 [SMILES: Clc1ccc(Br)cc1Cc1ccc(O[C@@H]2CCOC2)cc1]

Mass spectrum (ESI$^+$): m/z=366/368/370 (Br+Cl) [M]$^+$ (3) 4-bromo-1-chloro-2-(4-tetrahydropyran-4-yloxy-benzyl)-benzene

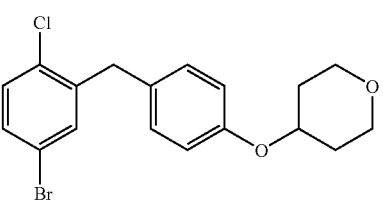 [SMILES: Clc1ccc(Br)cc1Cc1ccc(OC2CCOCC2)cc1]

(4) 4-bromo-1-chloro-2-(4-cyclohexyloxy-benzyl)-benzene

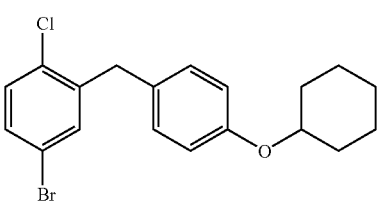 [SMILES: Clc1ccc(Br)cc1Cc1ccc(OC2CCCCC2)cc1]

(5) 4-bromo-1-chloro-2-(4-cyclobutyloxy-benzyl)-benzene

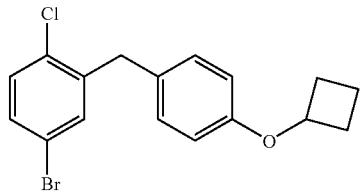 [SMILES: Clc1ccc(Br)cc1Cc1ccc(OC2CCC2)cc1]

Example X

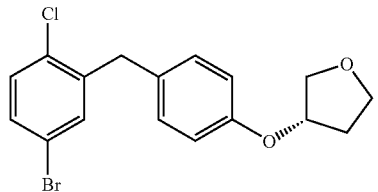

(S)-4-bromo-1-chloro-2-(4-tetrahydrofuran-3-yloxy-benzyl)-benzene

Variant A:

To a suspension of 250 g (5-bromo-2-chloro-phenyl)-{4-[(S)-(tetrahydro-furan-3-yl)oxy]-phenyl}-methanone in 1.33 L of acetonitrile and 314 mL of triethylsilane is added 93 mL of boron trifluoride diethyl etherate at 20° C. The solution is stirred at 20° C. for 16 hours. The mixture is filtered and the filtrate is quenched with 1.5 L of 1.5 M sodium hydroxide solution at 0 to 20° C. The solvent is removed upon evaporation and the residue is diluted with 1.3 L of methyl tert-butyl ether. The product is washed with 1.2 L of 0.1 M NaOH followed by 1 L of water. The solvent is removed upon evaporation and most of the triethylsilanol is removed upon the distillation of toluene.

Yield: 218 g (90% of theory)

Mass spectrum (ESI$^+$): m/z=368/370 (Cl) [M+H]+

Variant B:

To a suspension of 50.00 g (5-bromo-2-chloro-phenyl)-{4-[(S)-(tetrahydro-furan-3-yl)oxy]-phenyl}-methanone in 260 mL of acetonitrile and 34.68 g of dimethylethylsilane is added 20.45 g of boron trifluoride diethyl etherate at 20° C. The solution is stirred at 20° C. for 16 hours. The mixture is filtered and the filtrate is quenched with 290 mL of 1.5 M sodium hydroxide solution at 0 to 20° C. The solvent is removed upon evaporation and the residue is diluted with 260 mL of methyl tert-butyl ether. The product is washed with 240 mL of 0.1 M NaOH followed by 200 mL of water. The solvent is removed upon evaporation and most of the dimethylethylsilanol is removed upon the distillation of heptane.

Yield: 45.76 g (95% of theory)

Mass spectrum (ESI$^+$): m/z=368/370 (Cl) [M+H]$^+$

Variant C:

To a suspension of 1.91 g (5-bromo-2-chloro-phenyl)-{4-[(S)-(tetrahydro-furan-3-yl)oxy]-phenyl}-methanone and 0.38 g of sodium borohydride in 10 mL of methylene chloride (or fluorobenzene alternatively) is added 5.92 g of trifluoroacetic acid at 0° C. The solution is stirred at 20° C. for 16 hours and quenched with 20 mL of water and 20 mL of MTBE at 0 to 20° C. The product is washed with 20 mL of water. The solvent is removed upon evaporation.

Yield: 1.6 to 1.75 g (87 to 95% of theory)

Variant D:

To a suspension of 1.91 g (5-bromo-2-chloro-phenyl)-{4-[(S)-(tetrahydro-furan-3-yl)oxy]-phenyl}-methanone and 0.8 g of sodium borohydride in 10 mL of isopropyl acetate is added 11.4 g of trifluoroacetic acid at 0° C. The solution is stirred at 20° C. for 16 hours and quenched with 20 mL of water and 20 mL of MTBE at 0 to 20° C. The product is washed with 20 mL of water. The solvent is removed upon evaporation.

Yield: 1.6~1.75 g (8795% of theory)

Variant E:

To a solution of 0.19 g (5-bromo-2-chloro-phenyl)-{4-[(S)-(tetrahydro-furan-3-yl)oxy]-phenyl}-methanone in 5 mL of tetrahydrofuran is added 0.04 g of sodium borohydride at 20° C. The solution is stirred at 20° C. for 16 hours and the solvent is exchanged to 5 mL of methylene chloride. To the slurry is added 0.35 mL of 1 M boron trichloride methylene chloride solution, 0.02 mL of water and 0.24 mL of trifluoroacetic acid at 0° C., respectively. The mixture is stirred at ambient temperature for 4 hours and quenched with 10 mL of water and 10 mL of MTBE at 0 to 20° C. The product is washed with 10 mL of water. The solvent is removed upon evaporation.

Yield: 0.18 g (97% of theory)

Example XI

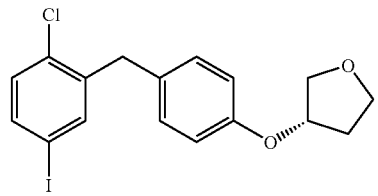 [SMILES: Clc1ccc(I)cc1Cc1ccc(O[C@H]2CCOC2)cc1]

(S)-4-iodo-1-chloro-2-(4-tetrahydrofuran-3-yloxy-benzyl)-benzene

Variant A:

To a suspension of 63.12 g (2-chloro-5-iodo-phenyl)-{4-[(S)-(tetrahydro-furan-3-yl)oxy]-phenyl}-methanone in 300 mL of acetonitrile and 40.14 g of dimethylethylsilane is added 23.66 g of boron trifluoride diethyl etherate at 10° C. The solution is stirred at 20° C. for 16 hours. The reaction is quenched with 350 mL of 1.5 M sodium hydroxide solution at 0 to 20° C. The product is diluted in 200 mL of ethyl acetate. The product is washed with 200 mL of water. The solvent is removed upon evaporation and crystallized in 1:2 acetonitrile/water.

Yield: 54.9 g (90% of theory)

Mass spectrum (ESI$^+$): m/z=414/416 (Cl)[M+H]$^+$

Variant B:

To a solution of 0.22 g (2-chloro-5-iodo-phenyl)-{4-[(S)-(tetrahydro-furan-3-yl)oxy]-phenyl}-methanone in 5 mL of tetrahydrofuran is added 0.04 g of sodium borohydride at 20° C. The solution is stirred at 20° C. for 16 hours and the solvent is exchanged to 5 mL of methylene chloride. To the slurry is added 0.35 mL of 1 M boron trichloride methylene chloride solution, 0.02 mL of water and 0.24 mL of trifluoroacetic acid at 0° C., respectively. The mixture is stirred at 20° C. for 4 hours and quenched with 10 mL of water and 10 mL of MTBE at 0 to 20° C. The product is washed with 10 mL of water. The solvent is removed upon evaporation and crystallized in 1:2 acetonitrile/water.

Yield: 0.18 g (86% of theory)
Mass spectrum (ESI+): m/z=414/416 (Cl)[M+H]+

Example XII

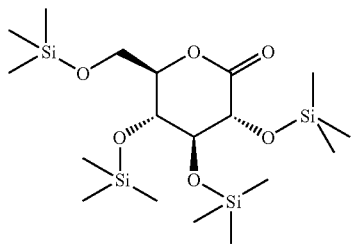

2,3,4,6-tetrakis-O-(trimethylsilyl)-D-glucopyranone

A solution of 20 g D-glucono-1,5-lactone and 98.5 ml N-methylmorpholine in 200 ml of tetrahydrofuran is cooled to −5° C. Then 85 ml trimethylsilylchloride are added dropwise so that the temperature does not exceed 5° C. The solution is then stirred for 1 h at ambient temperature, 5 h at 35° C. and again for 14 h at ambient temperature. After the addition of 300 ml of toluene the solution is cooled in an ice bath, and 500 ml of water are added so that the temperature does not exceed 10° C. The organic phase is then separated and washed with aqueous sodium dihydrogen phosphate solution, water, and brine. The solvent is removed in vacuo, the residue is taken up in 250 ml of toluene, and the solvent is again removed completely.

Yield: 52.5 g (approx. 90% pure)
Mass spectrum (ESI+): m/z=467 [M+H]+

Example XIII

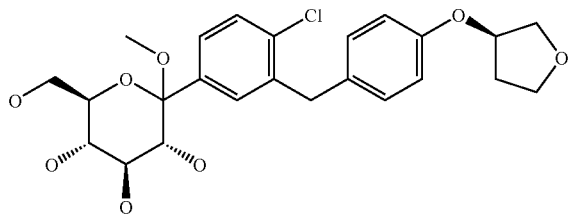 [SMILES: COC1(c2ccc(Cl)c(Cc3ccc(O[C@@H]4CCOC4)cc3)c2)O[C@H](CO)[C@@H](O)[C@H](O)[C@H]1O]

1-Chloro-4-(1-methoxy-D-glucopyranos-1-yl)-2-(4-(R)-tetrahydrofuran-3-yloxy-benzyl)-benzene A solution of 5.40 g (R)-4-bromo-1-chloro-2-(4-tetrahydrofuran-3-yloxy-benzyl)-benzene in 85 mL dry diethylether is cooled to −78° C. under argon. 18.5 mL of a 1.7 M solution of tert-butyllithium in pentane are slowly added dropwise to the cooled solution, and then the solution is stirred for 45 min at −78° C. Then a −78° C.-cold solution of 7.50 g (ca. 90% pure) of 2,3,4,6-tetrakis-O-(trimethylsilyl)-D-glucopyranone in 35 mL diethylether is added through a transfer needle.

The resulting solution is stirred for 2 h at −78° C., and then a solution of 2.5 ml methanesulfonic acid in 65 mL of methanol is added. The cooling bath is removed, and the solution is stirred for 16 h at ambient temperature. The solution is then neutralized with solid sodium hydrogencarbonate, most of the solvent is removed, and aqueous sodium hydrogen carbonate solution is added to the residue. The resulting mixture is extracted with ethyl acetate, the combined extracts are dried over sodium sulfate, and the solvent is removed to furnish the crude product that is submitted to reduction without further purification.

Yield: 6.95 g (crude product)
Mass spectrum (ESI+): m/z=503/505 (Cl) [M+Na]+

The following compounds may be obtained analogously to Example XIII:

(1) 1-Chloro-4-(1-methoxy-D-glucopyranos-1-yl)-2-(4-(S)-tetrahydrofuran-3-yloxy-benzyl)-benzene

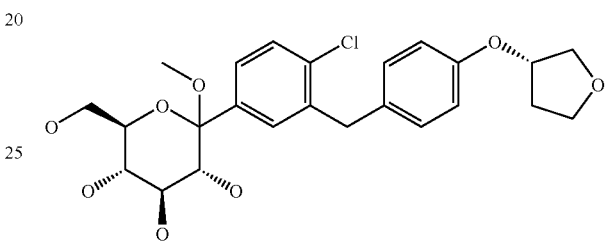

(2) 1-Chloro-4-(1-methoxy-D-glucopyranos-1-yl)-2-(4-cyclopentyloxy-benzyl)-benzene

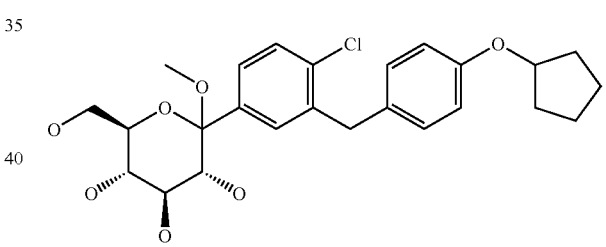

Mass spectrum (ESI+): m/z=501/503 (Cl) [M+Na]+

Example XIV

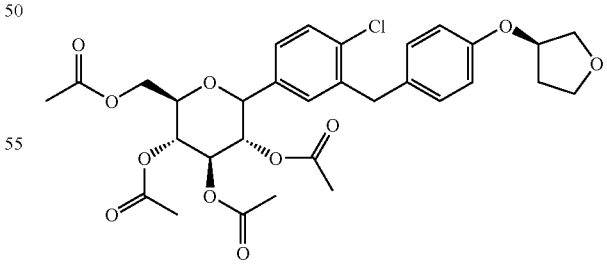

1-Chloro-4-(2,3,4,6-tetra-O-acteyl-D-glucopyranos-1-O-2-(4-(R)-tetrahydrofuran-3-yloxy-benzyl)-benzene A solution of 6.95 g 1-chloro-4-(1-methoxy-D-glucopyranos-1-yl)-2-(4-(R)-tetrahydro-furanyloxy-benzyl)-benzene and 4.7 mL triethylsilane in 40 ml dichloromethane and 80 ml acetonitrile is cooled to −10° C. Then 1.25 mL boron trifluoride etherate are added dropwise so that the solution temperature remained below 0° C. The solution is stirred for 3 h in an ice bath. Aqueous sodium hydrogen carbonate solution is added, and the resulting mixture is extracted with ethyl acetate. The organic phase is dried over sodium sulfate, the solvent is removed, and the residue is taken up in 80 mL dichloromethane. Then 8.5 mL of pyridine, 7.8 mL of acetic anhydride and 100 mg of 4-dimethylaminopyridine are added. The solution is stirred for 1 h at ambient temperature and then diluted with water. The mixture is extracted with dichloromethane, the organic phase is washed with 1 M hydrochloric acid and dried over sodium sulfate. After the solvent is removed the residue is recrystallized from ethanol to furnish the product as white crystals.

Yield: 2.20 g (25% of theory)

Mass spectrum (ESI⁺): m/z=619/621 (Cl) [M+H]⁺

The following compounds may be obtained analogously to Example XIV:

(1) 1-Chloro-4-(2,3,4,6-tetra-O-acteyl-D-glucopyranos-1-yl)-2-(4-(S)-tetrahydrofuran-3-yloxy-benzyl)-benzene

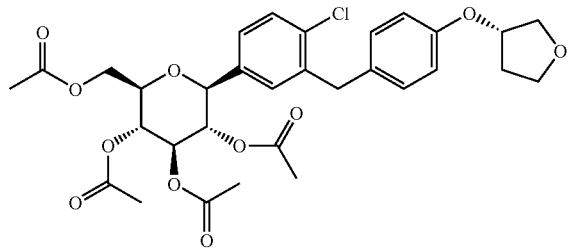 [SMILES: CC(=O)OC[C@H]1O[C@@H](c2ccc(Cl)c(Cc3ccc(O[C@H]4CCOC4)cc3)c2)[C@H](OC(C)=O)[C@@H](OC(C)=O)[C@@H]1OC(C)=O]

(2) 1-Chloro-4-(2,3,4,6-tetra-O-acteyl-D-glucopyranos-1-yl)-2-(4-cyclopentyloxy-benzyl)-benzene

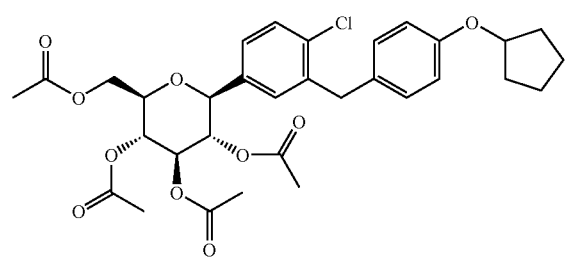 [SMILES: CC(=O)OC[C@H]1O[C@@H](c2ccc(Cl)c(Cc3ccc(OC4CCCC4)cc3)c2)[C@H](OC(C)=O)[C@@H](OC(C)=O)[C@@H]1OC(C)=O]

Mass spectrum (ESI⁺): m/z=640/642 (Cl) [M+Na]⁺

Example XV

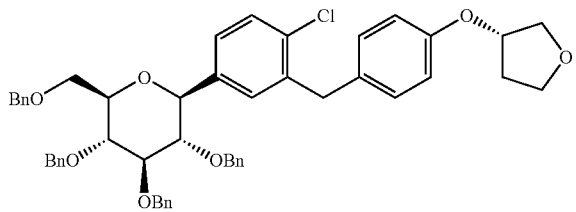 [SMILES: Clc1ccc([C@@H]2O[C@H](COCc3ccccc3)[C@@H](OCc3ccccc3)[C@H](OCc3ccccc3)[C@H]2OCc2ccccc2)cc1Cc1ccc(O[C@H]2CCOC2)cc1]

1-Chloro-4-(2,3,4,6-tetra-O-benzyl-D-glucopyranos-1-yl)-2-(4-(S)-tetrahydrofuran-3-yloxy-benzyl)-benzene A solution of 0.37 g 1-chloro-4-(1-methoxy-2,3,4,6-tetra-O-benzyl-D-glucopyranos-1-yl)-2-(4-(S)-tetrahydrofuran-3-yloxy-benzyl)-benzene and 0.21 mL triethylsilane in 2.5 ml dichloromethane and 7.5 ml acetonitrile is cooled to −20° C. Then 0.13 mL boron trifluoride etherate are added dropwise over 1 min. The resulting mixture is allowed to warm to −10° C. over 1 h. Aqueous sodium hydrogen carbonate solution is added, and the resulting mixture is extracted with ethyl acetate. The organic phase is washed with brine, dried over sodium sulfate, and concentrated under vacuum. The resulting residue was purified by column chromatography to give a mixture of alpha and beta isomers (alpha:beta ratio approximately 1:3) as a thick oil in quantitative yield.

Yield: 0.36 g (100% of theory)

Mass spectrum (ESI⁺): m/z=833/835 (Cl) [M+Na]⁺

Example XVI

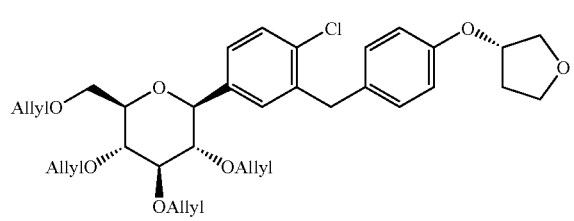

1-Chloro-4-(2,3,4,6-tetra-O-allyl-D-glucopyranos-1-yl)-2-(4-(S)-tetrahydrofuran-3-yloxy-benzyl)-benzene A solution of 0.37 g 1-chloro-4-(1-methoxy-2,3,4,6-tetra-O-allyl-D-glucopyranos-1-yl)-2-(4-(S)-tetrahydrofuranyloxy-benzyl)-benzene and 0.28 mL triethylsilane in 2.5 ml dichloromethane and 7.5 ml acetonitrile is cooled to −20° C. Then 0.16 mL boron trifluoride etherate are added dropwise over 1 min. The resulting mixture is allowed to warm to −10° C. over 1 h. Aqueous sodium hydrogen carbonate solution is added, and the resulting mixture is extracted with ethyl acetate. The organic phase is washed with brine, dried over sodium sulfate, and concentrated under vacuum. The resulting residue was purified by column chromatography to give a mixture of alpha and beta isomers (alpha:beta ratio approximately 1:9) as a thick oil.

Yield: 0.30 g (85% of theory)
Mass spectrum (ESI⁺): m/z=633/635 (Cl) [M+Na]⁺

Example XVII

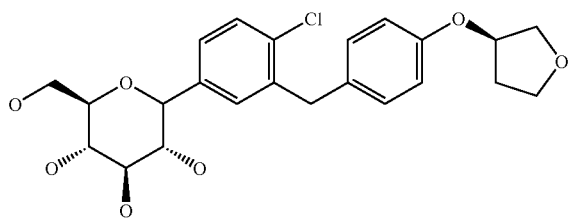 [SMILES: OC[C@H]1OC(c2ccc(Cl)c(Cc3ccc(O[C@@H]4CCOC4)cc3)c2)[C@H](O)[C@@H](O)[C@@H]1O]

1-Chloro-4-(β-D-glucopyranos-1-yl)-2-(4-(R)-tetrahydrofuran-3-yloxy-benzyl)-benzene To a solution of 2.20 1-chloro-4-(2,3,4,6-tetra-O-acetyl-D-glucopyranos-1-yl)-2-(4-(R)-tetrahydrofuran-3-yloxy-benzyl)-benzene in 30 mL of methanol is added 4 mL of 4 M aqueous potassium hydroxide solution. The solution is stirred at ambient temperature for 1 h and then neutralized with 4 M hydrochloric acid. The methanol is evaporated, and the residue is diluted with brine and extracted with ethyl acetate. The combined organic extracts are dried over sodium sulfate, and the solvent is removed. The residue is chromatographed on silica gel (dichloromethane/methanol 1:0→4:1).

Yield: 1.45 g (90% of theory)
Mass spectrum (ESI⁺): m/z=451/453 (Cl) [M+H]⁺

The following compounds may be obtained analogously to Example XVII:

(1) 1-Chloro-4-(β-D-glucopyranos-1-yl)-2-(4-(S)-tetrahydrofuran-3-yloxy-benzyl)-benzene

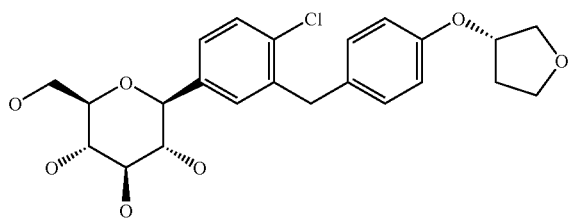 [SMILES: OC[C@H]1O[C@@H](c2ccc(Cl)c(Cc3ccc(O[C@H]4CCOC4)cc3)c2)[C@H](O)[C@@H](O)[C@@H]1O]

Mass spectrum (ESI⁺): m/z=451/453 (Cl) [M+H]⁺

(2) 1-Chloro-4-(β-D-glucopyranos-1-yl)-2-(4-cyclopentyloxy-benzyl)-benzene

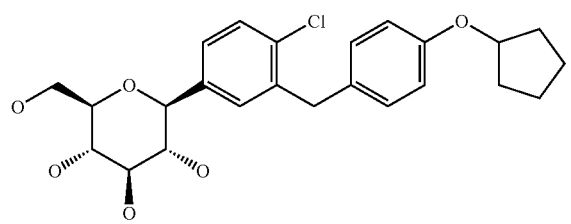 [SMILES: OC[C@H]1O[C@@H](c2ccc(Cl)c(Cc3ccc(OC4CCCC4)cc3)c2)[C@H](O)[C@@H](O)[C@@H]1O]

Mass spectrum (ESI⁺): m/z=466/468 (Cl) [M+NH₄]⁺

(3) 1-Chloro-4-(β-D-glucopyranos-1-yl)-2-(4-tetrahydropyran-4-yloxy-benzyl)-benzene

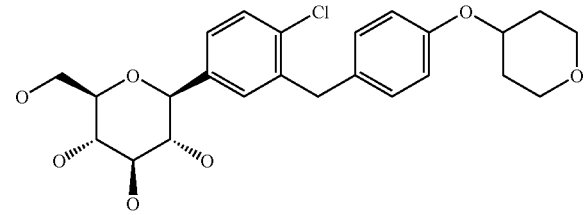 [SMILES: OC[C@H]1O[C@@H](c2ccc(Cl)c(Cc3ccc(OC4CCOCC4)cc3)c2)[C@H](O)[C@@H](O)[C@@H]1O]

Mass spectrum (ESI⁺): m/z=487/489 (Cl) [M+Na]⁺

(4) 1-Chloro-4-(β-D-glucopyranos-1-yl)-2-(4-cyclohexyloxy-benzyl)-benzene

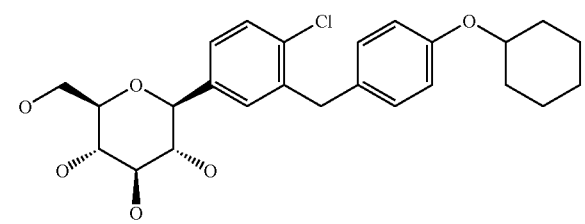 [SMILES: OC[C@H]1O[C@@H](c2ccc(Cl)c(Cc3ccc(OC4CCCCC4)cc3)c2)[C@H](O)[C@@H](O)[C@@H]1O]

Mass spectrum (ESI⁺): m/z=480/482 (Cl) [M+NH₄]⁺

(5) 1-Chloro-4-(β-D-glucopyranos-1-yl)-2-(4-cyclobutyloxy-benzyl)-benzene

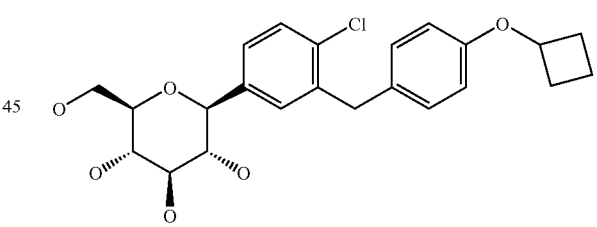

Mass spectrum (ESI⁺): m/z=452/454 (Cl) [M+NH₄]⁺

Example XVIII

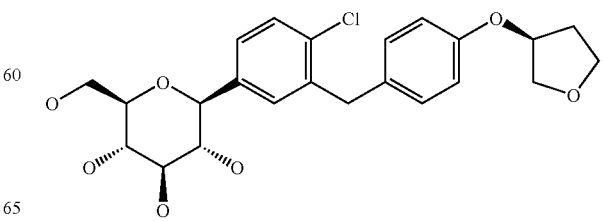

1-Chloro-4-(β-D-glucopyranos-1-yl)-2-(4-(S)-tetrahydrofuran-3-yloxy-benzyl)-benzene Variant A:
Step i)
To a solution of 5.5 mL 2.0 M BuMgCl in THF in 30 mL of tetrahydrofuran is added 12 mL of 2.5 M BuLi in hexane at −15 to −5° C. and stirred at −10° C. for 20 minutes. 10.00 g of (S)-3-[4-(5-bromo-2-chloro-benzyl)-phenoxy]-tetrahydrofuran in 10 mL of THF is added at −23 to −20° C. and stirred at −22° C. for 20 min. 20.32 g of 2,3,4,6-tetrakis-O-(trimethylsilyl)-D-gluco-pyranone in 7 mL of THF is added at −20 to −18° C. The reaction is then stirred at −20° C. for 1 hour and warmed to −12° C. in another hour. 60 mL of 25 weight-% aqueous NH$_4$Cl solution is added to quench the reaction. 40 mL of MTBE is added and the organic layer is separated. The aqueous layer is extracted with 30 mL of EtOAc. The combined organic phases are dried over MgSO$_4$ and concentrated.
Step ii)
The residue of step i) is dissolved in 100 mL of MeOH and 0.52 g of MeSO$_3$H and stirred at 43° C. for 4 hours. The reaction is then cooled to 5° C. and quenched with 20 mL of 10 weight-% NaHCO$_3$ aqueous solution. MeOH is distilled under reduced pressure and 25 mL of water and 25 mL of EtOAc are added. The organic layer is separated, and the aqueous phase is extracted with 20 mL of EtOAc. The combined organic phases are dried and concentrated to dryness.
Step iii)
The residue of step ii) was dissolved in 63 mL of MeCN and 43 mL of CH$_2$Cl$_2$ and cooled to −20° C. 7.59 g of triethylsilane is added, followed by addition of 6.95 g of boron trifluoride etherate. The reaction is warmed up gradually from −20 to 10° C. over 2 h. 40 g of 10 weight-% NaHCO$_3$ is added to quench the reaction. The organic solvents are removed under reduced pressure. 50 mL of isopropyl acetate and 12 mL of water are charged and the mixture is stirred at ambient temperature for overnight. The product is filtered and dried.
Yield: 13.5 g (55% of theory)
Mass spectrum (ESI$^+$): m/z=451/453 (Cl) [M+H]$^+$
Variant B:
Instead of BuMgCl in step i) of variant A i-PrMgCl is used. The steps ii) and iii) are as in variant A.
Variant C:
Instead of BuMgCl in step i) of variant A i-PrMgCl/LiCl is used. The steps ii) and iii) are as in variant A.
Variant D:
Step i)
To a solution of 2.90 g (S)-3-[4-(5-bromo-2-chloro-benzyl)-phenoxy]-tetrahydrofuran in 4 mL of THF at 0 to 20° C. (or alternatively at 20° C.), is slowly charged 8.4 mL of 1.0 M PrMgCl/LiCl in THF. The reaction is stirred at 20° C. for 16 hours and cooled to −23° C. 4.3 g of 2,3,4,6-tetrakis-O-(trimethylsilyl)-D-glucopyranone in 2 mL of THF is added dropwise. The reaction is then stirred at −20° C. for 2 h. Aqueous NH$_4$Cl solution (25 weight-%, 12 mL) is added to quench the reaction. MTBE (8 mL) is added and the organic layer is separated. The aqueous layer is extracted with EtOAc (30 mL). The combined organic phases are dried over MgSO$_4$ and concentrated.
Step ii)
The residue of step i) is dissolved in MeOH (20 mL) and MeSO$_3$H (260 mg, 2.8 mmol) and stirred at 43° C. for 3 h. The reaction is then cooled to 5° C. and quenched with 10 weight-% NaHCO$_3$ aqueous solution (12 mL). MeOH is distilled under reduced pressure and water (4 mL) and EtOAc (30 mL) are added. The organic layer is separated, and the aqueous phase is extracted with EtOAc (20 ml). The combined organic phases are dried and concentrated to dryness.
Step iii)
The residue of step ii) is dissolved in MeCN (17 mL) and CH$_2$Cl$_2$ (11 mL) and cooled to −20° C. Triethylsilane (2.08 g, 17.9 mmol) is added, followed by addition of boron trifluoride etherate (1.9 g, 13.4 mmol). The reaction is warmed up gradually from −20 to 10° C. over 2 h. 10% NaHCO$_3$ (25 mL) is added to quench the reaction. Organic solvents are removed under reduced pressure. Isopropyl acetate (15 mL) and water (5 ml) are charged and the mixture is stirred at ambient temperature for overnight. The product is filtered and dried.
Yield: 0.91 g (27% of theory)
Mass spectrum (ESI$^+$): m/z=451/453 (Cl) [M+H]$^+$
Variant E:
Step i)
To a solution of 2.90 g (S)-3-[4-(5-iodo-2-chloro-benzyl)-phenoxy]-tetrahydrofuran in 4 mL of THF at −23° C., is slowly charged 8.4 mL of 1.0 M i-PrMgCl/LiCl in THF. The reaction is stirred at −22° C. for 20 minutes. 4.3 g of 2,3,4,6-tetrakis-O-(trimethylsilyl)-D-glucopyranone in 2 mL of THF is added dropwise. The reaction is then stirred at −20° C. for 2 h. Aqueous NH$_4$Cl solution (25 weight-%, 12 mL) is added to quench the reaction. MTBE (8 mL) is added and the organic layer is separated. The aqueous layer is extracted with EtOAc (30 mL). The combined organic phases are dried over MgSO$_4$ and concentrated.
Step ii)
The residue of step i) is dissolved in MeOH (20 mL) and MeSO$_3$H (260 mg, 2.8 mmol) and stirred at 43° C. for 3 h. The reaction is then cooled to 5° C. and quenched with 10 weight-% NaHCO$_3$ aqueous solution (12 mL). MeOH is distilled under reduced pressure and water (4 mL) and EtOAc (30 mL) are added. The organic layer is separated, and the aqueous phase is extracted with EtOAc (20 ml). The combined organic phases are dried and concentrated to dryness.
Step iii)
The residue of step ii) is dissolved in MeCN (17 mL) and CH$_2$Cl$_2$ (11 mL) and cooled to −20° C. Triethylsilane (2.08 g, 17.9 mmol) is added, followed by addition of boron trifluoride etherate (1.9 g, 13.4 mmol). The reaction is warmed up gradually from −20 to 10° C. over 2 h. 25 ml aqueous 10 weight-% NaHCO$_3$ are added to quench the reaction. Organic solvents are removed under reduced pressure. Isopropyl acetate (15 mL) and water (5 ml) are charged and the mixture is stirred at ambient temperature for overnight. The product is filtered and dried.
Yield: 2.2 g (65% of theory)
Mass spectrum (ESI$^+$): m/z=451/453 (Cl)[M+H]$^+$

The invention claimed is:
1. Process for preparing the compounds of general formula V,

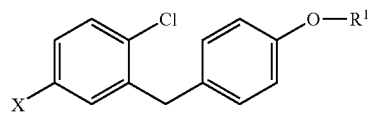

wherein
R$^1$ denotes R tetrahydrofuran-3-yl or S-tetrahydrofuran-3-yl; and
X denotes a bromine atom or a iodine atom;
said method comprised of the steps of reacting a benzoyl chloride derivative of the formula XII

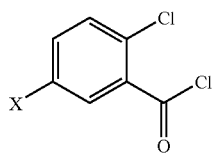

wherein X is defined as above; or a derivative thereof such as a benzoyl anhydride, an ester or a benzonitrile; with a halobenzene of the formula XXVII

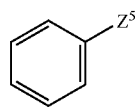

wherein $Z^5$ denotes a fluorine, chlorine or iodine atom; in the presence of a catalyst to obtain an intermediate compound of the formula XXVI

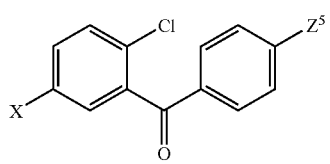

wherein X and $Z^5$ are defined as hereinbefore; and reacting the intermediate compound of the formula XXVI with $R^1$—OH, wherein $R^1$ is defined as hereinbefore, or an anion thereof, in the presence of a base to yield a benzophenone derivative of the formula VII

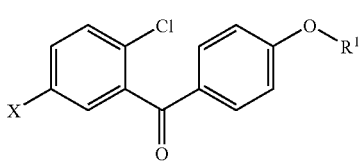

wherein X and $R^1$ are defined as hereinbefore; and the benzophenone derivative of the formula VII is reacted with a reducing agent in the presence of a Lewis acid to furnish the compound of the formula V as defined above.

2. Compound of general formula VI

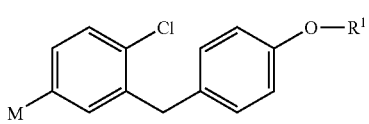

wherein $R^1$ denotes R tetrahydrofuran-3-yl or S-tetrahydrofuran 3-yl; and

M denotes Li or MgHal, wherein Hal denotes Cl, Br or I.

3. Compound selected from the group consisting of:

(S)-4-bromo-1-chloro-2-(4-tetrahydrofuran-3-yloxy-benzyl)-benzene;

(R)-4-bromo-1-chloro-2-(4-tetrahydrofuran-3-yloxy-benzyl)-benzene;

(S)-4-iodo-1-chloro-2-(4-tetrahydrofuran-3-yloxy-benzyl)-benzene; or (R)-4-iodo-1-chloro-2-(4-tetrahydrofuran-3-yloxy-benzyl)-benzene.

4. Compound of general formula VII

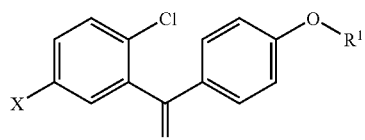

or of the formula XIX

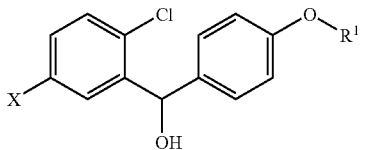

wherein $R^1$ denotes R tetrahydrofuran-3-yl or S-tetrahydrofuran 3-yl; and

X denotes Br or I.

5. Compound of the formula VII according to claim 4 selected from the group consisting of (5-bromo-2-chloro-phenyl)-(4-(R)-tetrahydrofuran-3-yloxy-phenyl)-methanone;

(5-bromo-2-chloro-phenyl)-(4-(S)-tetrahydrofuran-3-yloxy-phenyl)-methanone;

(5-iodo-2-chloro-phenyl)-(4-(R)-tetrahydrofuran-3-yloxy-phenyl)-methanone;

(5-iodo-2-chloro-phenyl)-(4-(S)-tetrahydrofuran-3-yloxy-phenyl)-methanone.

6. Compound selected from the group consisting of (5-bromo-2-chloro-phenyl)-(4-fluoro-phenyl)-methanone;

(5-iodo-2-chloro-phenyl)-(4-fluoro-phenyl)-methanone.

* * * * *